(12) United States Patent
Schaefer et al.

(10) Patent No.: US 8,121,388 B2
(45) Date of Patent: Feb. 21, 2012

(54) DEVICE AND METHOD FOR AUTOMATICALLY DETERMINING THE INDIVIDUAL THREE-DIMENSIONAL SHAPE OF PARTICLES

(75) Inventors: Michael Schaefer, Altrip (DE); Juergen Ettmueller, Hassloch (DE); Stefan Ziegler, Eusserthal (DE); Klaus Reindel, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 927 days.

(21) Appl. No.: 12/093,037

(22) PCT Filed: Nov. 16, 2006

(86) PCT No.: PCT/EP2006/068541
§ 371 (c)(1),
(2), (4) Date: May 8, 2008

(87) PCT Pub. No.: WO2007/060127
PCT Pub. Date: May 31, 2007

(65) Prior Publication Data
US 2008/0279448 A1    Nov. 13, 2008

(30) Foreign Application Priority Data
Nov. 23, 2005  (DE) .................. 10 2005 055 825

(51) Int. Cl.
*G06K 9/36*  (2006.01)
(52) U.S. Cl. ....................... 382/141; 382/154
(58) Field of Classification Search .............. None
See application file for complete search history.

(56) References Cited

U.S. PATENT DOCUMENTS

| | | | |
|---|---|---|---|
| 4,999,513 A | 3/1991 | Ito et al. | |
| 5,644,388 A | 7/1997 | Maekawa et al. | |
| 6,049,381 A | 4/2000 | Reintjes et al. | |
| 2002/0084172 A1* | 7/2002 | Toms .......................... | 198/445 |
| 2008/0019887 A1* | 1/2008 | Lohmann et al. ............. | 422/243 |

FOREIGN PATENT DOCUMENTS

| | | | |
|---|---|---|---|
| DE | 24 45 148 A1 | | 4/1976 |
| EP | 1 464 949 A2 | | 10/2004 |
| EP | 1 662 247 A1 | | 5/2006 |
| JP | 62168033 A | * | 7/1987 |
| WO | WO 02/11065 A2 | | 2/2002 |
| WO | WO 2005/062022 A1 | | 7/2005 |

OTHER PUBLICATIONS

V. Kachel, et al., "Uniform Lateral Orientation, Caused by Flow Forces, of Flat Particles in Flow-through Systems", The Journal of Histochemistry and Cytochemistry, vol. 25, No. 7, XP 002915897, ISSN 0022-1554, 1977, pp. 774-780.

* cited by examiner

*Primary Examiner* — Brian Werner
(74) *Attorney, Agent, or Firm* — Oblon, Spivak, McClelland, Maier & Neustadt, L.L.P.

(57) ABSTRACT

A method for automated determination of an individual three-dimensional shape of particles includes: a) dosing, alignment, and automated delivery of the particles; b) observation of the aligned particles and image acquisition, and c) evaluation of the images. A device for automated determination of the individual three-dimensional shape of particles includes: a) a mechanism for dosing, alignment, and automated delivery of the particles; b) at least two cameras for observation of the aligned particles, and c) a mechanism for evaluation of the images. The device can be used for automated determination of individual three-dimensional shape of particles.

18 Claims, 24 Drawing Sheets

Fig. 5 (Var. 1)

Fig. 6 (Var. 1`)

Fig. 7 (Var. 1b)

Fig. 8 (Var. 2)

Fig. 9 (Var. 2b)

Fig. 10 (Var. 2c)

Fig. 11 (Var. 3-2)

Fig. 12 (Var. 3-2b)

Fig. 13 (Var. 3-3)

Fig. 14 (Var. 3-4)

Fig. 15 (Var. 3-4b)

Fig. 16 (Var. 4)

Fig. 17 (Var. 5)

Fig. 18 (Var. 5b)

Fig. 24
1 
2 
3 
4 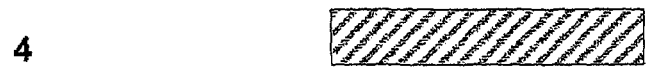
5 
6 
7 
8 
9 

DEVICE AND METHOD FOR AUTOMATICALLY DETERMINING THE INDIVIDUAL THREE-DIMENSIONAL SHAPE OF PARTICLES

The present invention relates to a method for automated determination of the individual three-dimensional shape of particles, comprising the following steps: a) dosing, alignment and automated delivery of the particles; b) observation of the aligned particles and image acquisition and c) evaluation of the images. The present invention furthermore relates to a device for automated determination of the individual three-dimensional shape of particles, comprising: a) means for dosing, alignment and automated delivery of the particles; b) at least two cameras for observation of the aligned particles and c) means for evaluation of the images; as well as to the use of the device according to the invention for automated determination of the individual three-dimensional shape of particles.

In the context of the present application, the term shape is intended to mean the spatial shape, i.e. on the one hand the shape of the particles in the mathematical sense, i.e. the description of the particle dimensions e.g. by geometrical dimensions (examples: length, diameter) and bodies (examples: sphere, ellipsoid, cylinder, cuboid) and their measurements, and on the other hand the "free" description (of the surface of the volume of arbitrary bodies) by finite surface elements such as triangles, or by discrete volume elements such as cubic voxels or other space lattice elements known from crystallography, or by spheres. These two shape descriptions in the narrower sense, whose approximation to reality is limited only by the resolution, is not to be confused with the form parameters often mentioned in the literature, which provide only incomplete and generally not physically interpretable information about the shape. The complete shape description (configuration) also yields the particle volume and the surface area and, derived therefrom, the apparent density, porosity, specific surface and all parameters describing the size and shape of the particles (the way in which these parameters can be determined for a known shape is known to the person skilled in the art). This method can furthermore be extended and additionally used for the simultaneous determination of surface properties such as the surface roughness and color (as well as color homogeneity) of particles, as well as for the detection of further adhering particles, surface defects and inclusions, and for the assessment of coating quality and homogeneity.

The particle shape, particularly in the case of arbitrarily shaped non-spherical particles, is an essential parameter for assessing the product quality and the behavior of such particles in the process. Particularly for bedding with arbitrarily shaped particles, the particle shape is an essential parameter. Such beds play an essential role in mechanical and chemical process technology. For instance, the behavior of beds is influenced essentially by the packing density of a system and its structure. The packing density and structure of a bed are in turn influenced essentially by the particle shape. The particle shape of arbitrarily shaped particles therefore has an essential influence e.g. on the achievable bed density, the dust settling behavior, the thermal conduction and pressure resistance beds through which there is a flow, the strength of aggregates and the drying behavior of filter cakes. The fundamental relationships between the shape and other particle properties, on the one hand, and product properties and process behavior are known to the person skilled in the art by the terms property function and process function (Schubert, Heinrich (editors); Handbuch der Mechanischen Verfahrenstechnik [Handbook of mechanical process technology], volume 1, chapter 2). In specific cases, they need to be determined by measurement techniques or calculated using models.

Precise, complete and unvitiated knowledge of the individual particle shape of arbitrarily shaped particles (i.e. the volume, the shape in the narrower sense, the size and the apparent density of the particles) are therefore prerequisites for the optimization of product properties and methods, as well as for simulation calculations at the particle level.

Methods are already commercially available which image particles and allow shape characterization on the basis of a projection surface in random orientation or in a stable position. These methods, referred to as two-dimensional shape description (2D), provide very limited shape information which cannot come close to fulfilling the aforementioned requirements.

For example, shape characterization of particles in a random orientation during freefall of the particles is known. Here, the Cam-Sizer® apparatus from Retsch will be mentioned as a generic example of a range of commercially available devices. It should be mentioned that the two cameras used in this apparatus serve only to extend the measurement range and not to improve the shape acquisition.

The Pharmavision® apparatus from Malvern will be mentioned as a generic example of devices for the analysis of particles which lie in a stable position on a substrate.

Lastly, methods are also known which align the particles in a flow cell and image them from one direction.

DE-A 24 45 148 relates to a device for aligning particles in a suspension, in particular a device for aligning generally flat particles in a position which is suitable for sampling them when they pass through a control device in a slotted shutter light measuring instrument.

Kachel V et al., Journal of Histochemistry and Cytochemistry, 25(7), 774 to 780, 1977 relates to a device for the uniform lateral orientation of flat particles in flow systems, the uniform orientation being achieved by flow forces.

For example, apparatus from Sysmex is commercially known.

A feature common to all these methods and apparatus is recording from one direction with a flat sensor, abbreviated here to 2D, which will not be considered in further detail since the invention relates to a 3D method and an apparatus with at least 2 observation directions.

In principle, various methods for the spatial (3D) imaging of particles are conceivable.

FIG. 1 represents possibilities for examining particles applied on a flat preparation.

According to FIG. 1, 3D analysis of particles deposited on a flat preparation can be carried out by observing them from a plurality of angles.

The prior art describes embodiments and methods according to FIG. 1 in which individual particles or smallish groups, which lie on a substrate, are imaged from three orthogonal directions. The three-dimensional shape is reconstructed from the three images obtained (e.g. R. Weichert and D. Huller: Volumenbestimmung und Formerkennung unregelmäBig geformter Partikeln mittels dreidimensionaler Bildanalyse [volume determination and shape recognition of irregularly shaped particles by means of three-dimensional image analysis]; Nuremberg, $2^{nd}$ Europ. Symposium Partikelmesstechnik (1979), pp. 266-272). This method provides good shape information for rounded particles, but the majority of the particles are recorded at unfavorable angles in the case of arbitrary non-rounded shapes, so that the actual shape remains hidden. Owing to the elaborate preparation and evaluation, furthermore, the method is economically viable only for very small particle numbers.

FIG. 2 represents possibilities for the on-line imaging (or automated imaging) of particles, which are based on the method of 3D image analysis as represented in FIG. 1 (observation at different angles).

According to FIG. 2A, 3D image analysis is carried out on particles which are in freefall.

According to FIG. 2B, 3D image analysis is carried out on particles aligned uniaxially on a turntable.

According to FIG. 2C, 3D image analysis is carried out on particles aligned uniaxially on an X/Y scanning stage.

Naturally, X-ray tomography is also an established method for recording the shape of objects. It is used both in medicine and in the manufacturing industry. Although X-ray tomography is the most complete conceivable shape information, the equipment and time outlay (and therefore the costs) are so great that this method cannot be used routinely in particle measurement technology.

For the description of particle collections, e.g. in the form of beds, large particle numbers have to be recorded for each sample, from several hundred to several thousand in the case of very similar, simply shaped particles, and from several thousand to tens of thousands in the case of particles which vary greatly in size or shape or are complexly shaped. The complete spatial shape of each particle must be recorded with a sufficient resolution, e.g. in a digitized representation.

It is therefore an object of the present invention to provide a method for automated determination of the individual three-dimensional shape of particles, wherein the individual three-dimensional shape of even complexly shaped particles can be determined in a short time so that this method can be applied in particle measurement technology.

This object is achieved by a method for automated determination of the individual three-dimensional shape of particles of samples in powder form or in the form of dispersions, wherein the following steps are carried out in succession:
a) individualized dosing of the particles, alignment of the particles in the longitudinal axis and automated delivery of the particles along a line;
b) observation of the aligned particles from at least two observation directions and image acquisition;
c) evaluation of the images.

The present invention furthermore relates to a device for automated determination of the individual three-dimensional shape (see above) of particles, comprising:
a) means for individualized dosing of the particles, means for alignment of the particles in the longitudinal axis and means for automated delivery of the particles along a predetermined line;
b) at least two cameras for observation of the aligned particles from at least two observation directions;
c) means for evaluation of the images.

DRAWING

The prior art and the invention will be explained in more detail with the aid of the drawing, in which.

Figure 2A:
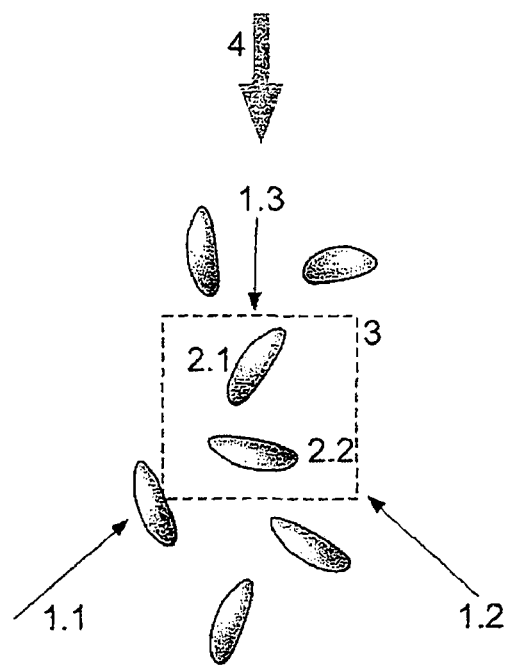
FIG. 2 shows possibilities for the on-line imaging (or automated imaging) of particles.
Figure 2B:
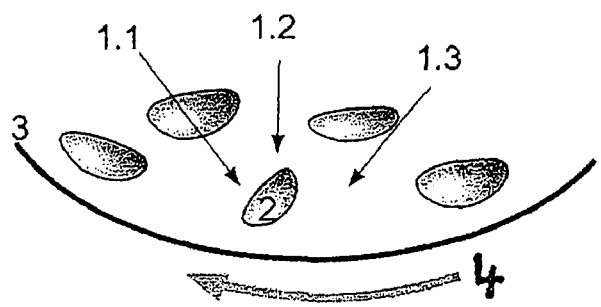

FIG. 2A: 3D image analysis of particles which are in freefall;

FIG. 2B: 3D image analysis of particles aligned uniaxially on a turntable.

Figure 2C:
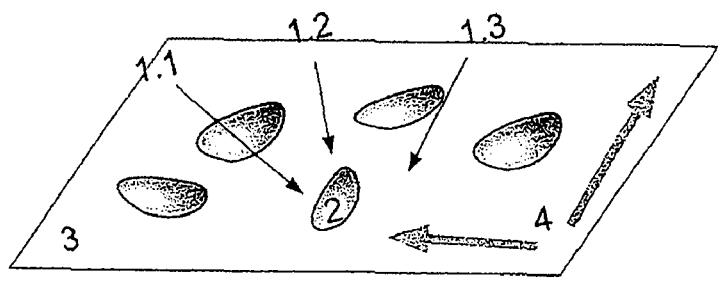

FIG. 2C: 3D image analysis of particles aligned uniaxially on an X/X scanning stage.

Figure 3:
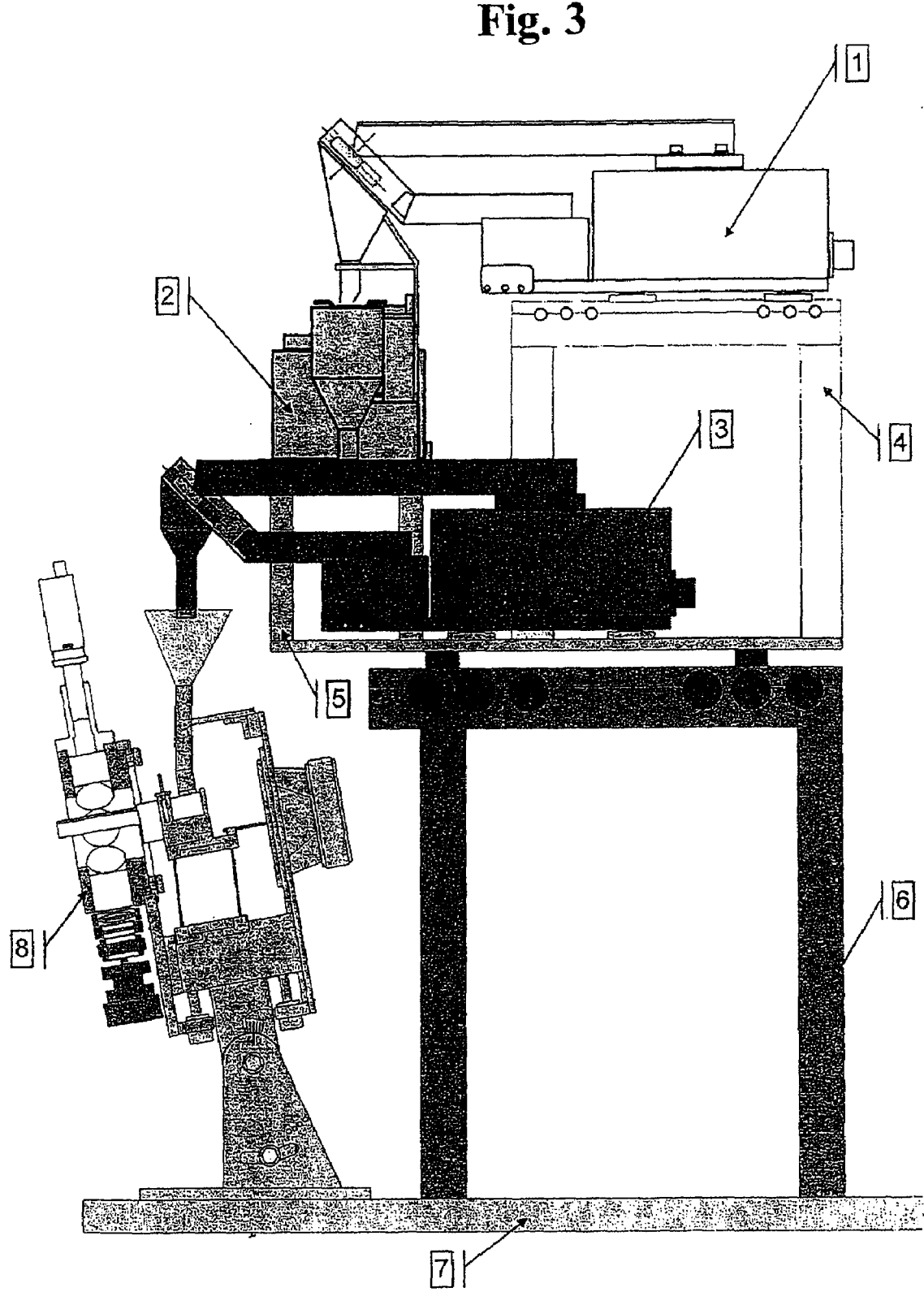
Figure 4:
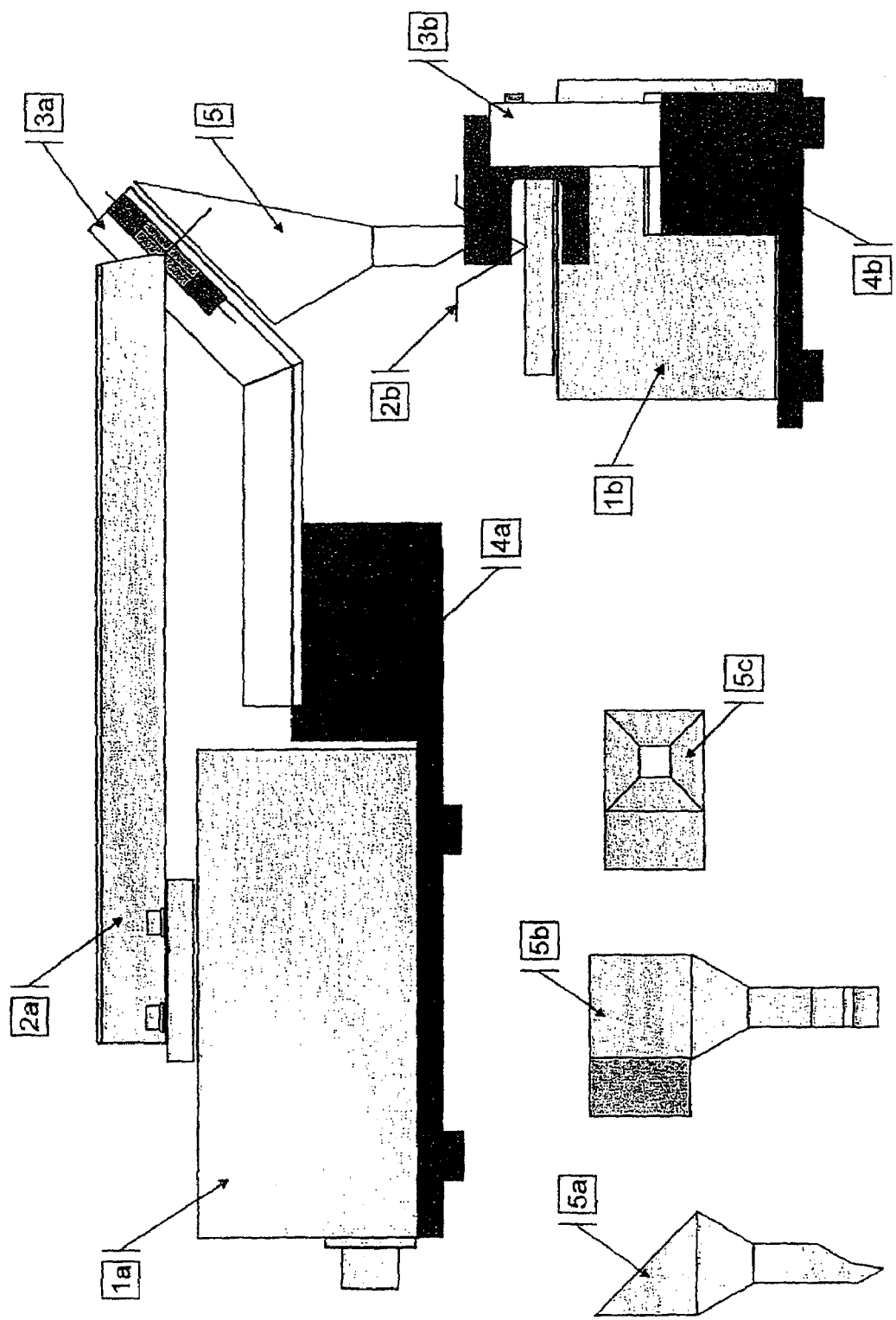
Figure 19:
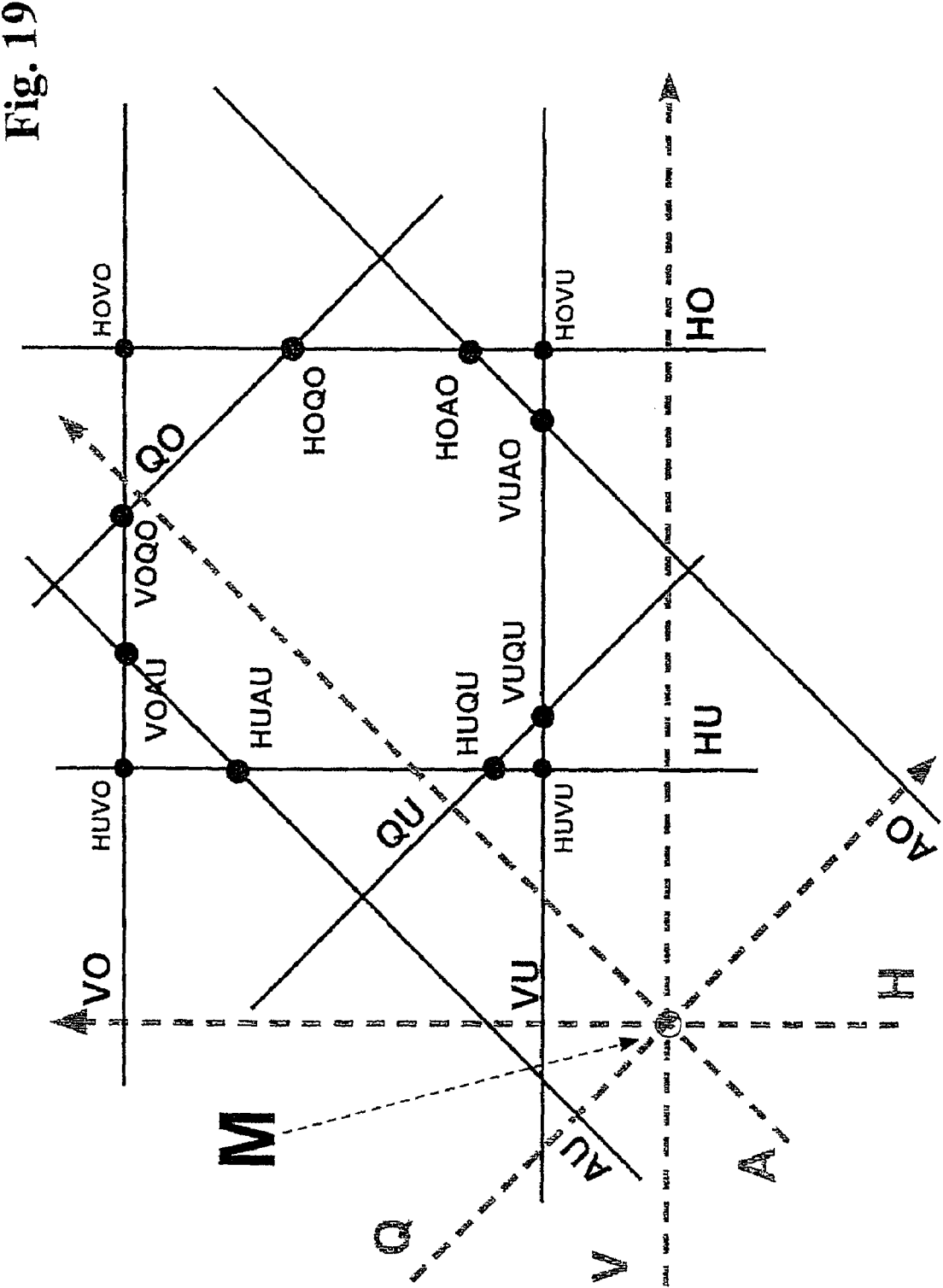
Figure 20:
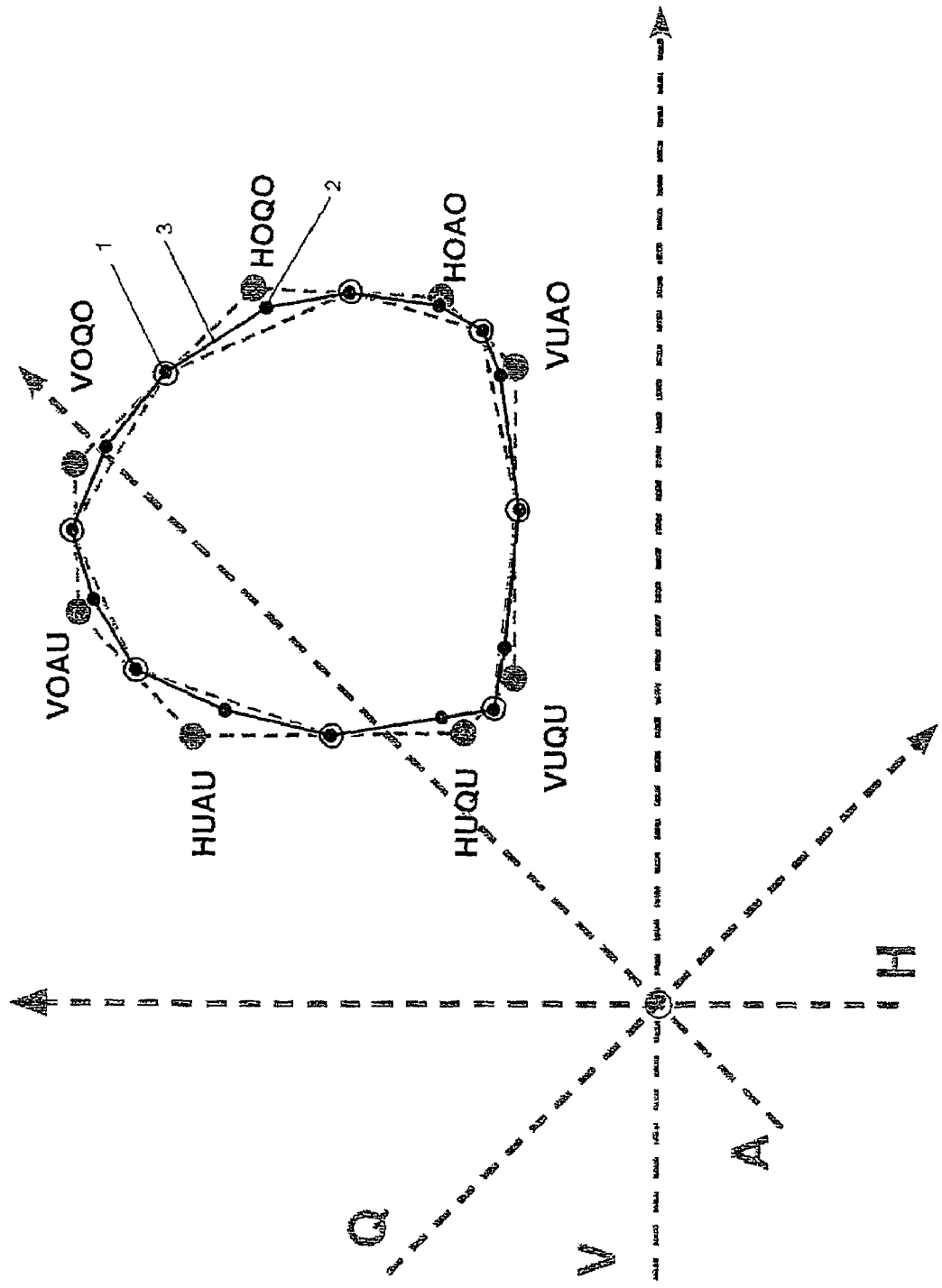
Figure 21:
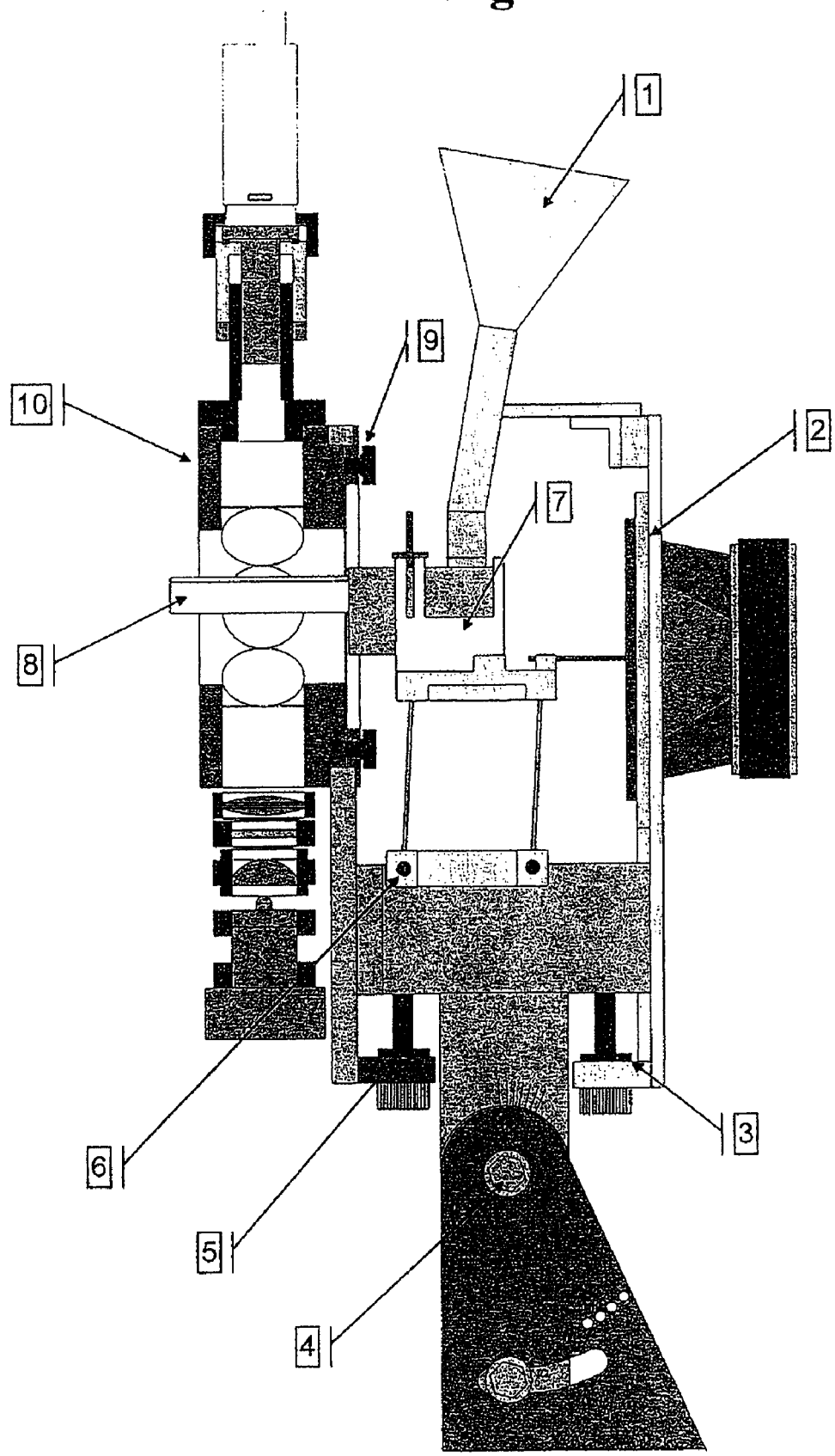
Figure 22:
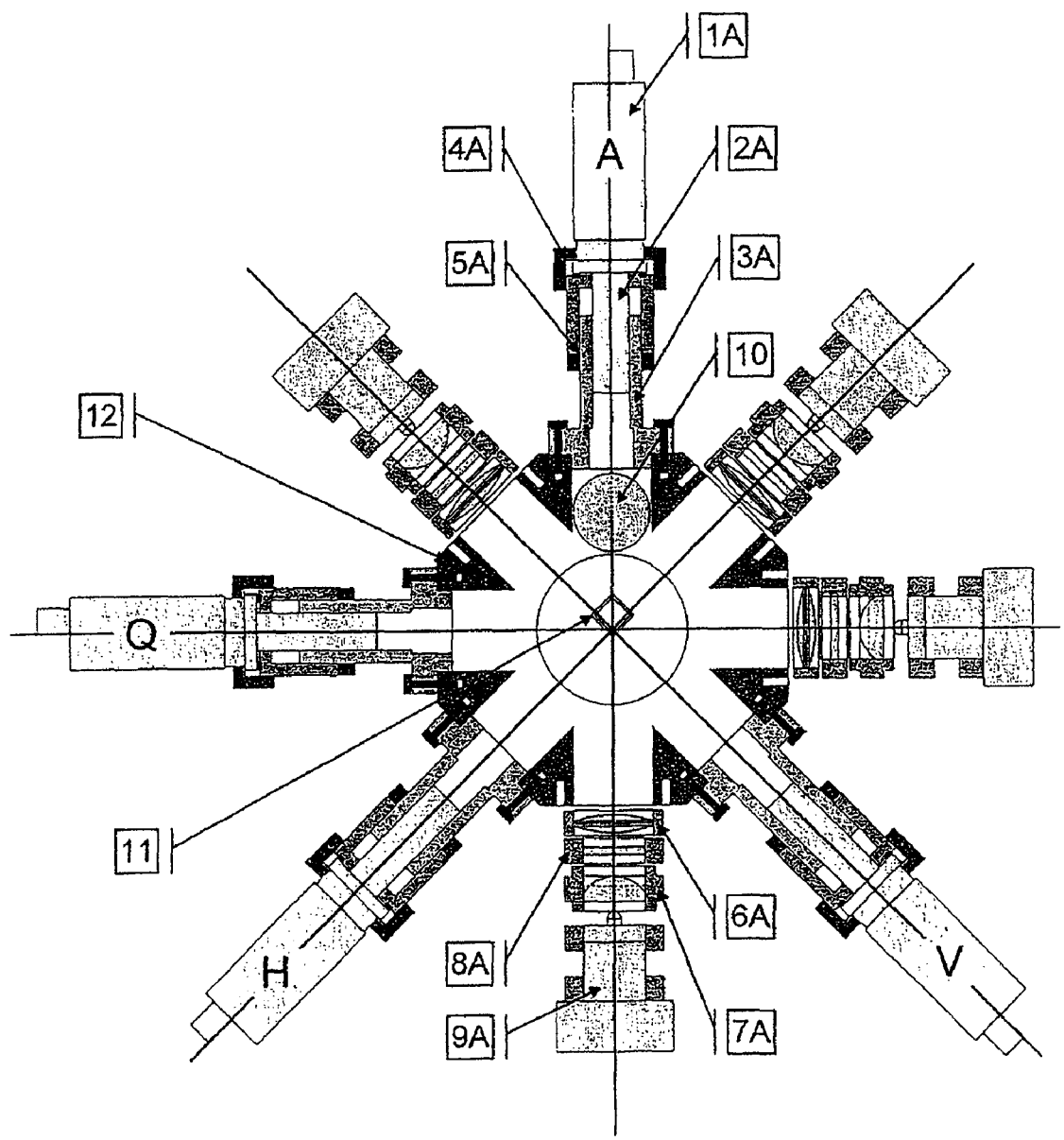
Figure 23:
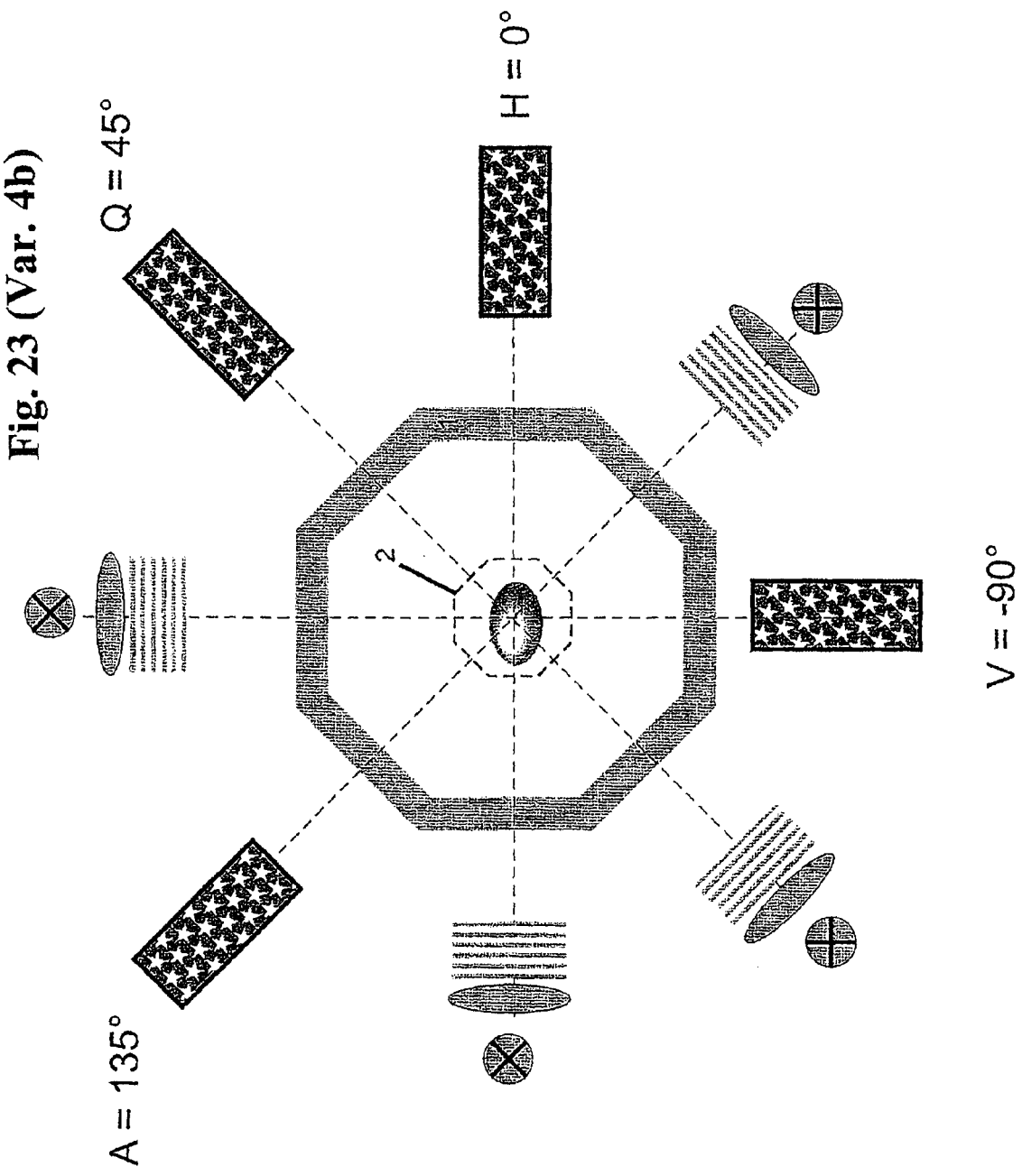

FIG. 3 shows an exemplary embodiment of a device according to the invention with dry delivery and 4 cameras (front view);

FIG. 4 shows an embodiment of a device according to the invention for dosing particles of powder-form samples and various views of a funnel for the product delivery;

FIGS. 5 to 18 and 23 show preferred embodiments of the invention with respect to delivery of the particles and the number, type and arrangement of the cameras used;

FIG. 19 shows a figure to explain the determination of intersection points between the observation beams in an embodiment with observation from 4 observation directions in order to determine the volume of an individual particle;

FIG. 20 shows a figure to explain the determination of the maximal, minimal and actual cross section of a slice lying at a defined position of an individual particle by describing the cross sections using octagons, in the embodiment represented in FIG. 19 with observation from 4 observation directions in order to determine the volume of an individual particle;

FIG. 21 shows an embodiment of the device according to the invention (front view);

FIG. 22 shows an embodiment of the device according to the invention (optics block, plan view);

FIG. 24 shows materials used in Variants 1 to 5 (FIGS. 5 to 18 and 23).

An overview of a device embodied according to the invention with dry delivery and 4 cameras is represented in FIG. 3.

With the aid of the method according to the invention or the device according to the invention, it is possible to record the three-dimensional shape of particles for large particle numbers in a short time, a representation being obtained with a sufficient resolution and handleable data quantity. Besides the individual three-dimensional shape of the particles, with the aid of the method according to the invention or the device according to the invention, special product properties (e.g. size ranges, form class, optical material properties and flowability) can furthermore be determined in special embodiments and special questions can be answered (e.g. shape, size, total volume, color).

a) Dosing, Alignment and Automated Delivery of the Particles

The processes of dosing, alignment and automated delivery may be carried out in succession. It is likewise possible for two or more of the processes to take place simultaneously. In a preferred embodiment, for example, the alignment and the automated delivery take place simultaneously, i.e. in one method step and by using a means for alignment and automated delivery.

When the term "sample" is used in what follows, this term in the scope of the present application means a multiplicity of particles to be studied. The sample may be present in various forms, as explained below.

The sample to be measured may be present in various forms, e.g. in the form of a powder or in the form of a dispersion, in which case the sample's particles to be analyzed are dispersed in a liquid. If the sample is comprised of flowable particles, i.e. particles which are individualizable and do not adhere to one another, then the determination according to the invention of the individual three-dimensional shape of the particles is generally carried out with the aid of the sample in the form of a powder. Many products are still flowable with particle sizes of about 20 µm, so that these samples can be studied in powder form. The exact limit as to whether or not a powder is flowable depends on the surface condition, the shape and the density of the particles. The relationships are known to the person skilled in the art. Very light or even tacky particles, which do not flow well, may be studied e.g. in the form of their dispersions.

The dosing, alignment and automated delivery of the particles, and corresponding means for dosing, alignment and automated delivery of the particles, depend on the form (e.g. powder form or dispersion) in which the sample is present. Suitable preferred embodiments and means for the dosing, alignment and automated delivery of particles in samples, which are present in various forms, will be mentioned below.

aa) Dosing

For dosing the particles, the particles are applied onto a delivery section for automated delivery of the particles. The mechanism for dosing and delivery (see below) may be the same.

Individualized dosing is carried out according to the invention. Here, the term "individualized" means that the individual particles of a sample to be analyzed, which contains a multiplicity of particles, are present separately from one another and are preferably put onto the delivery section individually, so as to permit observation of each individual particle of the sample in step b) of the method according to the invention. The conduct of the individualized dosing and suitable means for the individualized dosing depend inter alia on the form in which the sample is present.

i) Sample Present in Powder Form (Dry Delivery)

Various embodiments of individualized dosing are possible for dry delivery, the following embodiments being preferred:

ia) "Preset" Time Intervals

In one embodiment, the individualized dosing may be carried out so that respectively defined time intervals are set, a particle respectively being dosed at particular preset times. For example, presetting may be carried out such that one particle is respectively dosed per second. This timing is merely exemplary. In principle—as a function of the sample and other parameters—it is possible to preset arbitrary time intervals.

ib) "Random" Time Intervals

In another embodiment, the individualized dosing may be carried out so that particles are dosed at random time intervals. The time intervals depend inter alia on the type of dosing and the type of particles in the sample to be measured. The individual particles are not dosed at defined time intervals in this embodiment, rather the time intervals of the dosing of the individual particles may respectively be equal or different.

ic) "Particle on Demand"

In another embodiment, the particles can be dosed "on demand". A new particle to be measured may then be dosed respectively when a process, for example storing the data of the preceding particle or processing the data of the preceding particle, has been concluded ("on-line processing").

Embodiments ia) and ic) are preferred embodiments of the individualized dosing for dry delivery. Embodiment ic) is particularly preferred.

ii) Sample Present in the Form of a Dispersion (Wet Delivery)

For wet delivery, the individualized dosing of the particles is generally carried out at "random" time intervals (iib) as a function of the flow of the dispersion containing the particles through the flow cell being used.

Instead of delivering a dispersion containing the particles to be measured through the measurement cell, it is possible to guide the particles through a small thread of flow which is embedded in a flow through a larger opening (envelope stream). Suitable methods for achieving an envelope stream are known in the prior art. For example, the envelope stream technique is known from the application in cells known from the prior art for 2D image analysis. When using a coaxial envelope stream in order to draw the particle-carrying flow into a thread of flow lying centrally in the flow cross section, the product flow may be stopped after each recorded particle similarly as in dry dosing (while the envelope stream continues), in order to gain time for the storage and evaluation. These Variants iia (regular intervals) and iic (particle on demand) can be carried out by using computer-controlled pumps and valves. The risk that particles will catch up along the delivery section is also not so great with liquid delivery, so that it is also possible to employ small groups (2-5) by using a fast buffer memory (cf. image acquisition (method step b))).

In principle, it is possible to carry out dosing with a very small particle flow simply by setting the delivery rate of the particle flow, this method being suitable both for powder-form samples and for samples which are present in a dispersion.

In order to obtain reliable individualization of the particles, however, it is preferable to perform the dosing for powder-form samples so that each particle is deposited individually on the delivery section. Dosing channels are preferably used in order to dose powder-form samples. In a preferred embodiment, these have a V-shaped channel bottom which may optionally be rounded. It is particularly preferable to use two or more dosing channels connected in succession. The dosing of the individual particles onto the delivery section may, for example, be carried out with the aid of one or, preferably, two or more dosing channels connected in succession, preferably with light barriers. An embodiment in which the channel axis, gravitational force and light path lie in a plane, and the light barrier is preferably inclined for example by about 45°, is particularly preferred. The particles therefore always break the light barrier shortly after release from the channel, independently of the flight speed. For smaller particles of less than 1 mm, it is further preferred to reduce the rounding of the V-channel bottom to radii of between 100 and 500 µm, in order to center these small particles better. Suitable embodiments of light barriers and dosing channels are known to the person skilled in the art. In particular, it is known that the detection limit of a light barrier is generally from about $\frac{1}{10}$ to $\frac{1}{30}$ of the cross section, i.e. for example a diameter of 30 to 100 µm with a beam cross section of 1 mm. More particularly preferably, the particles are guided in a funnel for application onto the dosing channel respectively lying underneath, so that they are reliably collected and are deposited with the smallest possible collection speed and an advantageous direction (transverse to the delivery) onto the subsequent dosing channel or delivery channel, or measuring cuvette. In FIG. 4, details 5a, 5b, 5c represent a preferred embodiment of a funnel and its arrangement with respect to the dosing channels.

When only a small part of a large sample is to be evaluated, but it needs to be selected representatively and preliminary sample division is not desired, it is possible to integrate "in-line" sample division into the dosing and measure only a fraction of the sample, the remainder being diverted into a separate collection container.

Since the dosing, in particular powder-form dosing, is preferably carried out in multiple stages—with the aid of two or more dosing channels connected in succession, it is feasible e.g. for an electromagnetic valve, which switches constantly with programmed timing between release and retention, to be installed after the first dosing (from the storage container into the first dosing channel).

A suitable device for dosing particles of powder-form samples is represented in FIG. 4.

For wet delivery, i.e. in the case when the sample is present in the form of a dispersion, a dispersion of suitable concentration is generally prepared and pumped through a suitable measuring cuvette, which will be described in more detail below (circle or passage). The suitable concentration (starting from high concentrations) is then obtained when coincidences no longer occur and the images are qualitatively good enough for automatic recording. Excessively low concentrations are manifested by low particle account rates. When the sample is present in the form of a dispersion, the individualized dosing is generally carried out by dilution, the delivery by pumping and the alignment by shaping at the inlet of the measuring cell. The sample is also diluted by an envelope stream.

ab) Alignment

According to the invention, the longitudinal axis of the particles is generally aligned in the delivery direction (cf. "Delivery along a line" in ac). For dry delivery, all the particle axes are generally aligned by two bearing surfaces which influence them. Friction and gravitational force lead to the desired alignment. In the case of samples in the form of a liquid dispersion, a line in the scope of the present application is also intended to mean a streamline (thread of flow) which, in one embodiment, may be enveloped in an envelope stream. Owing to the alignment according to the invention, the individual three-dimensional shape of even complexly shaped particles can be determined in a short time. Because of the alignment of the particles along a line transverse to the observation direction, a maximal amount of information regarding the shape of the particles can be obtained with a minimal data set (number of images/observation directions), so that it is possible to apply the method according to the invention e.g. in particle measurement technology.

The particles' defined alignment according to the invention is of great importance. The simplest foreseeable case is an undefined and unknown alignment, e.g. in freefall or during transport in a liquid without an alignment feed. Accurate shape recording is not possible in this case, except in the unrealistic case that so many observation directions are recorded that they also include precisely those angles which are favorable for the particles in question. If the observation takes place transversely to the axis of least inertia, and along the other two, then the information gain is maximal.

In a preferred embodiment of the present invention, observation of the dry particles aligned on two surfaces takes place from two observation directions, generally with the aid of two cameras (see method step b)).

A right angle of the bearing surfaces and observation parallel to the bearing surfaces (and selected transversely to the delivery) are preferred in this embodiment.

In another particularly preferred embodiment of the present invention, observation of the aligned particles takes place from three or more, more particularly preferably from three or four, especially preferably from four observation directions (generally with the aid of a corresponding number of cameras) (see method step b)).

In this embodiment, with alignment of the particles in the longitudinal axis, sufficient information for accurate analysis of the particles is obtained. It should be noted that the other axes are also aligned by the bearing surfaces. The embodiment does not, however, require that the observation should take place only parallel to these surfaces.

The preferred methods and devices for dry alignment accordingly use the two bearing surfaces and the interaction of gravitational force and friction, as are set by the choice of the delivery parameters. For dry delivery, alignment in all axes is accordingly the rule since the other axes are generally co-aligned in order to align about the axis of least inertia. When bearing on only one surface, however, merely the axis of greatest inertia will be aligned perpendicularly to this surface ("stable position").

In a dry environment (generally for samples in powder form), the particles are as a rule in contact with two plane surfaces (bearing surfaces, cuvette walls) when they are drawn by gravitational force or centrifugal force in the direction of the intersection line of these surfaces. They will then become aligned in order to reach the state of least energy. The particles are preferably delivered along the intersection line of the two surfaces. These two bearing surfaces form the delivery channel (a curved channel is also possible as an alternative, for example with a circular, hyperbolic or parabolic profile). Besides the gravitational force, it is also possible to use centrifugal forces (see Variant 3-2b, FIG. 12). The optimal, i.e. more particularly preferred observation direction extends tangentially to the aligning bearing surfaces or cuvette walls. Particularly suitable embodiments relating to the optical implementation will be described below.

There are various possibilities for the shape of the bearing surfaces or cuvette walls. Precision cuvettes (hence also the term cuvette walls for the bearing surfaces) which are preferably square or rectangular, or V-channels, preferably 90° V-channels which may for example be produced by grinding such precision cuvettes on one side, are highly suitable. In the observation part, the free edges are preferably ground perpendicularly to the cuvette surfaces since these regions appear bright in the image. With other angles, e.g. 45°, these regions appear dark. As an alternative, it may be broken open only in the observation part so that the cuvette remains closed in subregions. Angles other than 90° may also be selected for the arrangement of the cuvette walls or V-channels. In this case, it should be noted that these surfaces must not interfere with the illumination and observation. With 2 angles (=two observation directions) it should preferably be possible to observe the particles tangentially to the respective bearing surface, so that the advantages of this most informative direction can be exploited. The further additional angles (=observation directions) will be presented further on. There are preferably as few edges, oblique or rough surfaces as possible in the observation direction, since these can cause interference. Variants 3-3 (see FIG. 13) and 3-4 (see FIG. 14) illustrate angles of 120°=2×60° (3 observation directions) and 135°=3×45° (4 observation directions).

The delivery channels, preferably precision cuvettes or V-channels, must not have plane-parallel sides. The inner surfaces or the crease between two surfaces, against which the particle is centered and aligned by the gravitational force or centrifugal force, can be configured independently of the outer surface. The subsurfaces of the delivery channels, preferably precision cuvettes or V-channels, need not necessarily be plane, tubes or a curved channel also being conceivable in principle. With a closed tube the imaging is distorted, however, although this can be compensated for e.g. by immersing the tube in an immersion liquid and externally bounding this with plane surfaces. These optical considerations also apply to all flow cuvettes (which are used for measuring samples in the form of dispersions). A constraint common to all the embodiments is that the objectives and their beam paths must have access to the particles in question.

In a preferred embodiment, particles of samples in powder form are thus aligned against one or more plane surfaces which form a delivery channel, with the aid of the gravitational force or with the aid of centrifugal forces.

Examples of suitable delivery channels, and illumination and observation systems adapted to them, are represented in FIGS. 5 to 18, which represent preferred embodiments of the present invention. The use of the delivery channels represented in these figures is independent of the special embodiment represented in the figures.

The above comments regarding the alignment of particles of samples in powder form with the aid of delivery channels relate to a preferred multiaxial alignment of the particles. As mentioned above, alignment of the axis of least inertia parallel to the delivery direction and transversely to the observation is always desired in the method according to the invention or the device according to the invention. The other two axes should also be aligned parallel to the observation in the case of two observation directions, although this is less important for observation from three or more observation directions. It should be noted that the proximity to the surface intersection line, or generally the line of least positional energy (see above), also causes the particles to become centered in the delivery line and therefore brought into the focal region of the observations, which is an intended and necessary effect.

The particles' alignment and centering according to the invention is preferably carried out by the gravitational force. Depending on the inclination of the profile (of the delivery channel), one bearing surface may be privileged by a greater normal component. Inclination angles of between 15° and 35° have been found to be advantageous. The additional alignment about the longitudinal axis (multiaxial alignment) is no longer so important for observation at 3 or more angles in a plane, but the alignment in the longitudinal direction is. It is then no longer necessary to privilege one bearing surface, although inclination in the direction of the crease is necessary for all the surfaces in order to ensure alignment and centering. In a relatively flat groove, the alignment direction itself will be more than 90°, e.g. 120° or 135°, although in this case both alignment angles are then very shallow and should preferably be selected to be equal.

The alignment of the particles of samples in the form of dispersions is preferably carried out by flow forces in a flow cell. A flow cell preferably used for the biaxial alignment of particles, which are present in a dispersion, is disclosed in the PCT application PCT/EP/2004/014603 entitled "High-accuracy flow-oriented multi-angle remission sensor" and will be explained in more detail below (see ac)).

Flow cells known from the prior art may furthermore be used for the uniaxial alignment of particles present in a dispersion, particularly for observation of particles from three or more observation directions. Similarly as in dry delivery, observation at 4 angles in an octagonal flow cell is preferred, particularly preferably in conjunction with an envelope stream for centering the particles in a thread of flow.

ac) Automated Delivery

The term delivery is used here for the portion of the particle transport which sends the particles through the observation volume. As already mentioned above, the delivery of the particles may take place simultaneously with the alignment of the particles and optionally also simultaneously with the dosing.

For wet delivery (e.g. of dispersions), the sample is preferably delivered through the flow (e.g. by means of a pump or a pressure gradient), generally with an upstream biaxial alignment volume in the case of 2 observation directions, and uniaxial in the case of 4 observation directions, the latter particularly preferably with an envelope stream. Design considerations will be found below.

For dry delivery, the sample (e.g. in powder form) can be slid along a line (for example in an oscillating delivery channel) along an intersection line of two surfaces forming a delivery channel (slip operation) (gradient driving force and/or vibration delivery) or deposited on a moved intersection line of two surfaces forming a delivery channel (entraining, e.g. rotating delivery channel) and subsequently removed (entrained delivery).

Three parameters, which may be combined, are available for delivery in slip operation by means of a vibrating delivery channel. On the one hand gradient driving, and on the other hand the vibration of the channel with excursion and longitudinal movement. For round particles which are inclined to roll, the gradient driving is preferably selected to be small. The vibration is adjusted by the vibration angle, the frequency and the amplitude. A preferred possibility for suspending the delivery channel so that it can oscillate (vibrate) is a double elastic band drive with inclination of the elastic bands, so that the arrangement exerts an excursion. With perpendicular bands, however, the excursion is zero. An electromagnet may for example be used as the drive, for example a compact, long-excursion bass loudspeaker, to the vibration coil of which a thrust rod that drives the delivery channel is fastened. A frequency generator (e.g. a separate device or a D/A card in the PC) with a power amplifier drives the loudspeaker in a preferred embodiment with an adjustable frequency (in the normal case the resonant frequency of the arrangement) and amplitude (these adjustment and embodiment possibilities are known to the person skilled in the art, and some of them can be performed by commercially available dosing devices). A sinusoidal movement is always obtained when driving at the resonant frequency, although other movement shapes may also be imposed with a corresponding driving force in nonresonant operation. Sliding delivery is generally adjusted by adapting the inclination angle and the excursion (angle and amplitude of the delivery). To this end, for example, the sliding surface may be composed of relatively short, straight subsurfaces, e.g. of widely available optically compatible cuvettes. The components of excursion force and gravitational force are generally parallel in the plane perpendicular to the delivery directions, other angles being possible but not offering any advantages.

The delivery channel which is used for slip operation therefore generally has an inclination angle of from 0 to 25° in the longitudinal direction (delivery direction). There is no generally preferred angle, since this is a product-dependent parameter which must be determined experimentally. A tried and tested value for beginning this adaptation lies between 7 and 10°.

In the transverse direction (perpendicularly to the delivery direction), the delivery channel generally has an inclination angle of from 0 to 45°. The preferred range is 15 to 35° for systems with 2 observation directions, and 45° is preferred for systems with 4 observation directions since this is the easiest to set.

Although entrained deliveries are very attractive, they must nevertheless be designed circularly or annularly in the delivery direction, or as a flexible band (cf. a band saw). It is very difficult to configure this so that the required optical properties are still obtained at the observation site. Specific embodiments relating to entrained delivery will be described below (Variant 3, see FIGS. 11 to 15, Variant 5b, see FIG. 18). The use of the delivery channels relating to entrained delivery represented in these figures is independent of the special embodiment represented in the figures.

After observation of the aligned particles, they are generally removed from the delivery channel. In most embodiments, the particle falls "by itself" into a collection container after the delivery section (at the end of the delivery channel), which is advantageous for subsequent weighing. Otherwise, e.g. with entrained deliveries, the particles may be scraped, brushed or sucked off, e.g. with delivery in a centrifugal field (Variant 3-2b, FIG. 12).

Lastly, the influence of the product on the product delivery should also be considered. Many products are still flowable with particle sizes of e.g. 50 μm, and can therefore be delivered by a channel. The limit depends on the surface condition, the shape and the density. The relationships are known to the person skilled in the art, since the handling of products is a standard task in process technology. Very light or even tacky particles, which do not flow well, may be delivered e.g. by a device according to Variants 3 and 5 (see FIGS. 11 to 15 and 18).

The dimensions of the product delivery channels and the magnification scales can be adapted to the particle size. There is in principle no upper limit, and 20 to 300 μm can be regarded as a lower limit for dry delivery (sample in the form of powder) depending on the product. For wet delivery (Variant 4, see FIG. 16) in the form of dispersions, which is recommendable for handling non-flowable particles, particles can be detected beyond about 2 μm, and first shape information can be sensibly obtained beyond about 5 μm. With the aid of the method according to the invention or the device according to the invention, the individual three-dimensional shapes of particles with different particle sizes can therefore be determined beyond a particle size of about 5 μm.

Various materials can be used as materials for the delivery channels (dry delivery). What is important is that observation of the particles is possible. When using a "closed" delivery channel, for example in the form of a cuvette or a tube, it is preferable to use transparent materials such as glass, polymer, ceramic, sapphire, diamond. When using "open" delivery channels, e.g. V-channels, other materials may be used besides the transparent materials which have been mentioned above, e.g. white, diffusely scattering materials (e.g. milk glass, white plastic, polytetrafluoroethylene, ceramic), mirrors, both 100% mirrors and semitransparent mirrors, and opaque materials such as metals. Suitable materials which have the above properties, and can be used as delivery channels in the method according to the invention or the device according to the invention, are known to the person skilled in the art. Further comments about materials preferred for particular embodiments will be made below (see bac)).

The automated delivery of particles of samples which are present in the form of a dispersion, which is preferably carried out in a flow cell, is preferably carried out by means of a pump or a pressure gradient.

A flow cell conventionally used for the alignment and measurement of particles of samples, which are present in the form of a dispersion, generally ends in a cuvette. The cuvette for measuring the aligned particles may be square or hexagonal or octagonal. Which of these designs is preferred depends essentially on the application. Availability/price, optical resolution, alignment outlay and accuracy of the volume and shape detection must be weighed up. If they have not been described above, these evaluations are known to the person skilled in the art (for example resolving power). It should be noted that these transparent cuvettes must have an optical quality and invisible joins on all surfaces (a suitable joining technique is known in the prior art, e.g. from Hellma).

Transparent materials, in particular glass and the other materials mentioned above, are suitable as materials for cuvettes.

The ratio of depth of focus and cross section of the cuvette for wet delivery is preferably not less than 1:10. This constraint is obviated when using an envelope stream. Commercially available square cuvettes of optical quality (precision cuvettes) have a minimal cross section of about 1 mm*1 mm. Cuvettes with smaller cross sections and wall thicknesses are likewise advantageous—given suitable availability (e.g. 0.5 or 0.2 mm).

A particularly preferably used—aforementioned—measuring cell, which is preferably used when studying samples in the form of dispersions (flow cell), allows two-dimensional alignment of the particles of the sample and is disclosed e.g. in the PCT application PCT/EP/2004/014603 entitled "High-accuracy flow-oriented multi-angle remission sensor". It is a three-dimensional flow cell for aligning non-isometric particles in a liquid sample in two axes, comprising a feed zone for the sample containing particles to be aligned and an outlet for the sample containing particles aligned in two axes, a fluid element of the sample with the dimensions a, b, c being converted in a stretching zone into a fluid element with the dimensions a×n, b/(n×m), c×m, where a denotes the width, b denotes the height and c denotes the length of the fluid element, and n and m are constants (degree of stretching) depending on the geometry of the flow cell, which denote positive numbers $\geq 1$. When applied to this situation, the cross section must be stretched in one direction in the flow part so that the entry gap becomes narrower than the cuvette cross section by this ratio. Very narrow cross sections are difficult to manufacture, and are also susceptible to clogging if individual particles are too large. However, even transverse stretching of 1.5, 1.8 or 2.0 is sufficient for the purpose of 3D measurement. The longitudinal stretching is not critical in design terms, and may be selected to be from 2 to 5.

As already mentioned above, instead of passing a dispersion containing particles to be measured through the measuring cell, it is possible to pass the particles through a small thread of flow which is embedded in a flow through a larger opening (envelope stream). Uniaxial alignment is generally achieved with the aid of said thread of flow. In one embodiment, therefore, the envelope stream can be used whenever the aligned particles are observed from three or more observation directions. It is in principle possible to employ an envelope stream when using all the cuvettes mentioned above. An envelope stream which extends only in the longitudinal direction (uniaxially) is preferably employed when using hexagonal or octagonal cuvettes.

b) Observation of the Aligned Particles with the Aid of at Least Two Cameras and Image Acquisition, Recording being Carried Out for all Images on which Particles are at Least Partially Imaged After the image acquisition, it is possible to process i.e. evaluate a selected image set of a particle directly and subsequently measure the next particle, or firstly store the selected image set of a particle without further evaluation and measure the next particle after storage. The evaluation is then carried out, for example, following the measurement and storage of the corresponding image sets of all particles of a sample. In a preferred embodiment, direct processing of the image set of a particle is carried out before the next particle is "called" for measurement ("particle on demand").

ba) Observation baa) Number of Observation Directions Used

Owing to the projection surface perceptible by it, each observation direction places an upper limit on the maximum volume which the observed particle can occupy, and a lower limit on the smallest volume. If the number is 1, then this involves a 2D shape description known from the prior art. This version does not limit the volume, since it does not provide any information in depth. Volume determination in 2D shape description is possible only for spheres.

According to the present invention, the number of observation directions is at least 2, preferably 2, 3 or 4, particularly preferably 4 (Variants 2, 2b, 2c). All embodiments with 2, 3, 4 or more observation directions lead to a delimited volume. In general, the number of cameras corresponds to the number of observation directions. It is then possible to make a comparison between the greatest and least convex shapes that fit the projection surfaces. The smaller the difference is, the less is the maximally possible error in the volume determination. The error can be reduced greatly by an expedient alignment of the particles, as is carried out according to the invention.

bab) Angle Between the Observation Directions

If two cameras are used, i.e. the number of observation directions is 2, then the angle between the observation directions is preferably 90° since this is the angle with the greatest information gain. The cameras are therefore preferably aligned mutually orthogonally when using two cameras.

With three or more directions, the observation directions may respectively be orthogonal to one another. Generally, however, this is not the particularly preferred arrangement (see Variant 5, 5b). Other angles may also be preferred depending on the alignment of the particles, for example 4 observations arranged at 45° intervals in a plane perpendicular to the transport direction (delivery direction) (Variants 2, 2b, 2c). In a preferred embodiment with 3 or more, preferably 3 or 4 observation directions, the angles of the observation directions lie in a plane perpendicular to the delivery direction of the particles.

Each observation direction has a plane of optimal focus, and a depth of focus range lying parallel to this plane. If all the observation directions lie in a plane, then the intersection of the focal planes gives a line, or a tube of the depth of field around this line. With 3 or more observation directions which do not lie in a plane, the optimal focus is reduced to a point or to a small volume around this point. As is known to the person skilled in the art, the depth of focus depends on the resolution of the imaging and, for smaller particles, is only of the order of the particle size. This means that in the general case particles only can be detected along a line ("string of beads") or at precisely one point. The particles' alignment according to the invention (see step ab)) not only leads to orientation of the axes of the particles in favorable directions, but also causes centering of the particles in a defined position so that their path follows the focal line or extends through the focal point. This is of great advantage since a time-consuming autofocus can thereby be obviated. The version with a focal line is particularly advantageous since in general it can obviate stopping the movement or triggering the image acquisition (see below).

bac) Type of Optical Imaging

Various types of optical imaging are possible, e.g. extinction transmitted light (ETL=directed illumination), diffuse transmitted light (DTL), coaxial direct light (CDL, usually with polarization) or concentric direct light ZDL).

The nature of the optical imaging is firstly distinguished as follows: extinction transmitted light (ETL=directed illumination), known from arrangements with telecentric objectives which use a plane illumination wave. For simple objectives with divergent observation (which may be preferred for reasons of space or cost) it is possible to set up convergent directed illumination which provides almost equivalent results. The other possibilities are diffuse transmitted light (DTL), coaxial direct light (CDL, usually with polarization) or concentric direct light ZDL) as mentioned above. The advantages and disadvantages of these imaging variants are generally known to the person skilled in the art (cf. "1D und 2D Abbildende Prozesssonden: Theorie und Praxis" [1D and 2D imaging process probes: theory and practice] lecture by Dr M. Schäfer to the Technical Committee of Particle Measuring Technology on Jan. 23, 2005 at Wurzburg). When used for multiaxial imaging and automatic evaluation, it should be noted that the imaging must allow automatic detection of the particle surface. This means that on the one hand it must be possible to distinguish unequivocally between the background and the particle projection surface. For an embodiment in ETL and DTL, the particles appear dark before a bright background, with particular richness in ETL. Parts of the projection surface may appear bright in the case of transparent particles, but in ETL the contour is always closed and the bright regions are very small so that the projection surface can be filled in with the algorithms known to the person skilled in the art in order to fill holes. It should be taken into account that in ETL, illumination must in any event be carried out through the surfaces used for aligning the particles or for guiding the liquid flow.

The observation and illumination being on opposite sides, it is firstly equivalent whether the observation is applied above or below the transparent guide plane. For DTL, the bearing surface itself may be transparent and illuminated through by the diffuse light, or it may be made of a scattering material with appropriate thickness (e.g. milk glass, white plastic, polytetrafluoroethylene) which is back-lit. The observation need not necessarily take place perpendicularly to the glass surface through which illumination is carried out. For ZDL and CDL, a dark background is generally selected in front of which the particles stand out brightly. It is also possible to select a bright background for dark particles, although this should preferably be illuminated so that no shadows are cast. All DL arrangements can have problems with transparent particles, i.e. other arrangements are preferably selected for transparent particles. In CDL, it is moreover possible to adopt a mirror as the background, exact perpendicular observation without polarization, in which case a "pseudo-ETL_image" is obtained with similar properties, particularly in respect of transparent particles.

Measurement of the particles' color is generally carried out in direct light. Observation directions are therefore recommended which are not aligned perpendicularly to the delivery channel (e.g. 135° or 45°, see Variants 2b and 2c, FIG. 10) and avoid specular reflection.

In all arrangements, it should be noted that the illumination responsible for one observation direction must not interfere with a different observation. Illumination from a plurality of directions is favorable in the case of direct light, since it avoids shadows. On the other hand, diffuse illumination from a plurality of directions can light up white particles so much that they can scarcely be detected.

It is therefore particularly preferable to use ETL. The optical quality is no problem with cuvettes as delivery channels, while profiles cannot so readily be produced with optical quality for rotation cylinders, bands and channels. This limitation can nevertheless be mitigated if the illumination is guided only through the materials used (for example plastics, foils, hot-formed glasses, transparent ceramic) and the observation is placed on the particle side (when using a delivery channel which is open, i.e. for example has a V-profile).

bad) Camera and Light Source

The specific choice of the camera and light source depends on the type of illumination. In general, particularly with transmitted light and all arrangements with centering (e.g. all the preferred embodiments (all variants) mentioned below other than Variant 4, FIG. 22, see below), a triggerable B/W camera with VGA resolution, with analog image transmission (preferably: progressive scan), a multichannel frame grabber with e.g. 4 simultaneous channels and illumination with a cold light source, white light LED (color LEDs are also feasible for transmitted light, and even advantageous for certain materials) or halogen lamps are used. White light LEDs, e.g. 1 W Lumileds from Luxeon, are advantageous owing to the compact structure and the vibration-insensitivity. Numerous other variants, which are likewise usable, may nevertheless be implemented by the person skilled in the art e.g. USB cameras, cameras with digital output, Cameralink, FireWire, etc.

The cameras may be produced in CCD and CMOS technology, the lower light strength of CMOS not being a problem for transmitted light except at high resolutions, when the shutter time is no longer sufficient in order to reduce the motion blur (the relationship between motion blur and exposure time is known to the person skilled in the art), in which case on the one hand CCDs may be adopted or stronger light sources (e.g. 3 W or 5 W diodes, cold light sources) or flash lamps (e.g. Wotan from Polytec). For direct light images, it is generally necessary to use a more sensitive camera and/or a brighter light source. Color cameras are sensible only when a direct light image with color information is required. For example, 3 B/W cameras in ETL and one color camera in CDL are then an expedient combination for 4 images. It should be noted that larger information quantities then need to be shifted, which makes the acquisition slower. The same argument also applies against higher-resolution cameras, which in principle offer lower image rates. In the embodiment represented in Variants 4 and 4b, (see FIGS. 16 and 23), it is preferable to use higher-resolution cameras since only a part of the image can be used in this case, and moreover not all the particles flowing through the flow cross section can be detected. Unique counting (each particle exactly once) is not compulsory for all applications, although it is desirable when the recorded volume is to be used with the weight of the sample in order to determine the apparent density (see also point bae)).

To this end, the length of the delivery section (image detail), delivery speed and image rate must be matched so that each particle is seen fully at least once. For example, 25 images/sec may be taken. All cameras which can be operated synchronously are suitable in principle for in-time acquisition of the images (see bae) and bbb)); otherwise the particle movement must be stopped at the correct moment, which is not always practicable and is slow in any case.

bae) Time Restriction

Since the particles are delivered continuously, two constraints are preferred in order to obtain particularly good results:

On the one hand, the exposure time should be so short that no motion blur is created. For medium imaging scales and a strong-power ETL arrangement, this is already possible with continuous light and shutter operation of the camera. A flash lamp may be used as an alternative for higher resolutions. It is then possible to divide the flash between a plurality of illuminations.

The following aspects apply with respect to the time and the frequency of the images in order to achieve optimal results when using the method according to the invention. Even if the dosing of the particles is actively controlled (individually, "particle on demand"), the time at which the particle lies in the middle of the image cannot be predicted accurately. With arrangements which do not lie in a plane and therefore have only a focal point, it is therefore difficult to find the time at which the particle is focused precisely for all observations. The possibility of selecting the good images from high-speed recording (1 per direction!) is feasible, although not preferred owing to the concomitant data stream. In principle, triggering may be carried out with a light barrier shortly before the measurement site.

Implementation is much simpler, and therefore particularly preferred, when all the observations lie in a plane. All the images then have the same longitudinal axis, and it is not important where exactly the particle lies at the time of the imaging. It is merely preferable to ensure that the recordings take place often enough so that each particle is fully detected at least once, if unique counting is required (i.e. an image set of at least one image per observation direction is applied for each dosing). Owing to incompleteness of the dosing and fragmenting or disaggregation, however, two or more particles may even pass through simultaneously or with a slight time offset.

bb) Image Acquisition bba) Imaging Scale

The imaging scale is given by the chip size of the camera, it being preferable to use a CCD or CMOS camera which generally lies between 0.25 and 1 inch, the pixel number of the camera (0.3 to 4 megapixels are now customary) and the magnification factor of the optics. There is no lower limit on this, the term macro-objectives being used in the range of from 0.1 to 1 and micro(scope) objectives above about 1 to 100. Higher-resolution objectives generally have working distances so small that it is technically impossible to image the same point simultaneously from different directions, since the objectives would then be in one another's way (slimly constructed probe designs are physically possible, but not economically viable). Other than in pure size measurement, for which very small pixel numbers (considered as the length of a particle) of 2-10 may already be satisfactory, much more resolution is needed for shape description. This depends on the complexity of the respective shape, although target values of the order of generally from 10 to 200 pixels are reasonable, preferably from 50 to 200 pixels.

bbb) Image Selection for Processing and/or Storage

It is advantageous to process and/or store only those images which actually show particles, and to discard empty images. It is sufficient to inspect one of the camera images as to whether it holds at least one particle. Only then will it be stored and/or evaluated. Since particles which touch the edge must also be discarded, this can be ascertained simultaneously.

There are a plurality of strategies for the further procedure. All the image sets are preferably first stored rapidly in the working memory and, after a reasonable waiting time (from 0.1 to 3 sec, depending on the product) when no more stragglers are to be expected, an image set is selected for evaluation and/or storage on data media.

Release for the next dosing preferably does not take place until all of the previous tasks have been concluded. In case of great urgency, however, the call may actually start somewhat earlier when the end of the processing is foreseeable. In the general case, multiple imaging or coincidences (2 or more particles simultaneously) will be processed in time-uncritical post processing. Since 3D evaluation provides the best criteria for double detection, evaluation after each dosing is preferred. It is then possible to select from a plurality of image sets according to suitable criteria, for example the image set with the smallest volume of particles or with the greatest number of different particles. (i.e. the set in which two coincident particles can be identified as separate.)

Depending on the hardware used, however, it may also be desirable to store all the images or only roughly preselected images.

The aim for storage is always to maximize the data rate, which requires a compromise between compressive preprocessing and writing speed on the disk. The methods for this are known to the person skilled in the art. In principle, the data streams can be simplified as early as possible and distributed between various frame grabbers, interfaces, processors and hard disks. Double-buffered image triggering, image exposure, image transmission, image processing and image storage are also advantageous. Image rates of the order of 40 ms are therefore generally possible, but slower in simple systems or even much faster (e.g. 5-10 ms) when using more powerful hardware. These images can be recorded in various, sometimes compressed recording methods (file formats such as TIFF, JPEG, AVI). For well-known materials, for example, the respective image may already be binarized with a threshold in the camera driver or on the frame grabber, so that up to 8 individual binary images can be stored in the 8 bits of a conventional 8-bit image with 256 gray levels. It is no longer necessary to form a gray threshold in the subsequent processing in this case, rather the individual levels must be extracted, although this is likewise carried out with a threshold operation. A B/W or color image optionally obtained in direct light must be stored as a gray or color image so that it can be evaluated later.

c) Evaluation of the Images ca) Preprocessing of the Image Data

Optionally, depending on the premises on which the recording is based, the stored image sets—or with direct processing (evaluation) the image sets obtained at the end of the image preselection—are preferably also preprocessed. The following operations may be carried out both beforehand and subsequently:

- Threshold formation (binary image as gray or color image or from the bit level, see above)
- Image cleaning (erosion, dilatation, discarding dust particles in the image)
- Filling holes (e.g. for transparent particles)
- Discarding marginal particles
- Discarding double-counted particles
- Multiple imaging of a particle can be eliminated by likelihood considerations. All the detected particle properties and the time and position of the detection can be used as a criterion. Since the particles always move forward, a particle e.g. which surfaces "upstream" must always be a new one. The tolerances for deciding whether a particle is "new" must be adapted to the differences between the particles and the likelihood that dosing may actually provide more than one particle (the best criteria are provided by the orientation-independent 3D parameters, see the comments under bbb))
- Extracting contour (binary image) and color information from a direct light image
- The binary image must be detected with threshold formation (contour for reconstruction) and at the same time the color inside this contour must be determined (average values, standard deviations and distribution of gray levels, or colors, e.g. in the RGB or HSL system (or in other color spaces known to the person skilled in the art).
- Discarding particles with unfavorable placement (see also the selection criteria under bbb)
- Reducing particle images individually to an expedient resolution
- Dividing up images of coincidences (see above)

In general, the sample delivery is designed so that only one particle is respectively deposited and double events (or multiple events, also referred to as coincidences) are rare. Many double events are detected because two particles are actually found simultaneously in the image field, or differ significantly.

cb) Reconstruction of the Volume

All the methods known to the person skilled in the art may be used in order to reconstruct and represent the individual three-dimensional shape of the particles (3D bodies) from the projection images obtained in step b) and optionally processed in step ca), for example Weichert, R., Huller, D.: Volumenbestimmung und Formerkennung unregelmäßig geformter Partikeln mittels dreidimensionaler Bildanalyse [volume determination and shape recognition of irregularly shaped particles by means of three-dimensional image analysis]; Nuremberg, $2^{nd}$ Europ. Symposium Partikelmesstechnik (1979), pp. 266-272. It should be mentioned that the respectively visible projection surfaces delimit a spatial body; respectively following an observation direction, all the image regions in which no particle is visible could be "ground away". Although this is correct, it is mathematically complex and very time-consuming. On the other hand, a reconstruction according to the invention using the concept of "slices", which is explained in more detail below, is very efficient and preferred.

The reconstruction of the volume is particularly accurate for entirely convex bodies. Bodies with concave portions can be recorded only limitedly by projection surfaces, it being necessary to distinguish in the spatial region between uniaxial and biaxial concave portions. A "hole", whose depth cannot be recorded from any lateral direction, is biaxially concave. Uniaxially concave portions, i.e. "trenches" and cuts, can be recorded from the suitable perspective. An example which may be mentioned here is a double sphere whose cut can be seen into fully in a lateral view (spheres next to each other), while it remains hidden in a front view.

Figure 5:
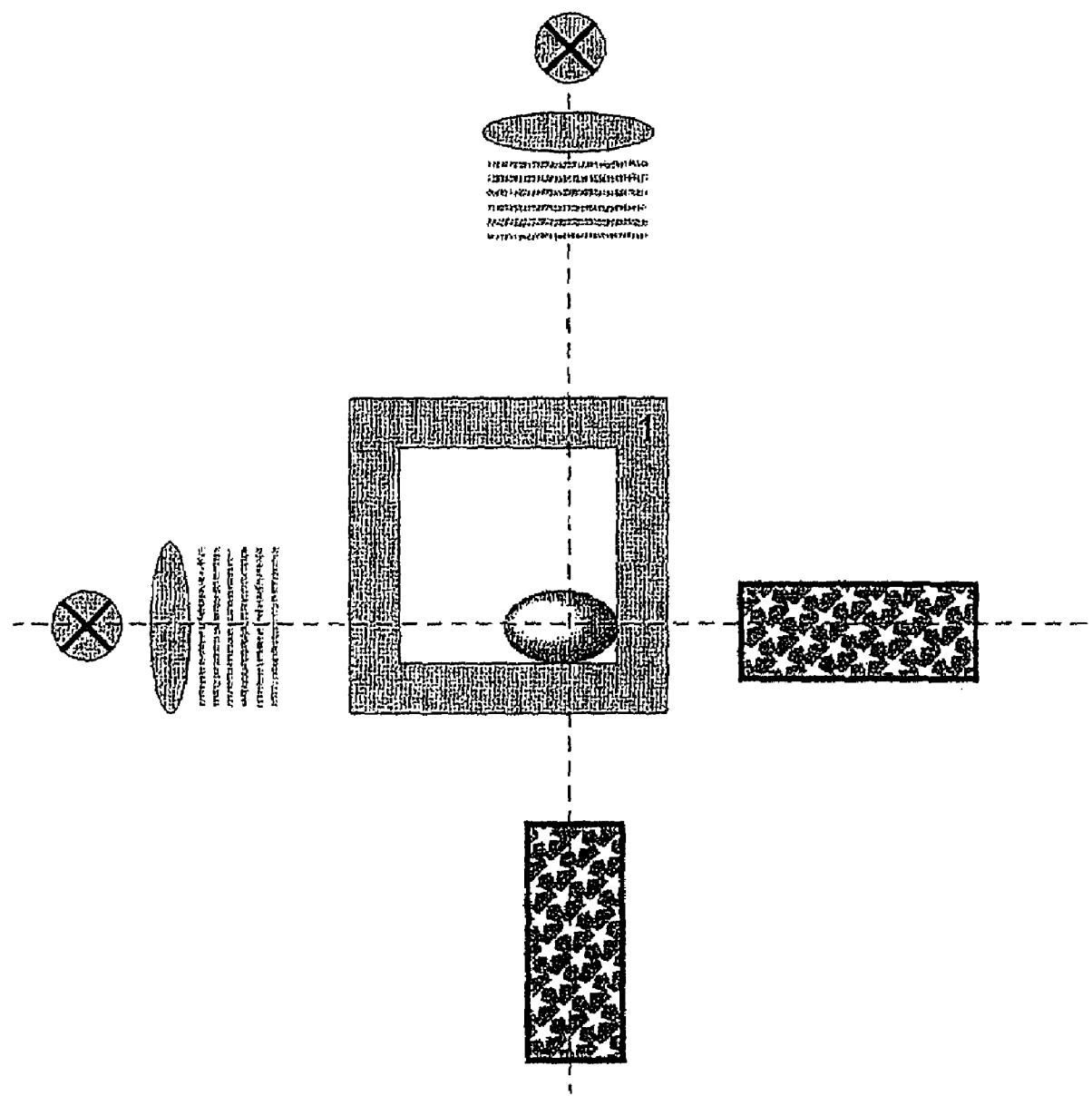

All observations which take place in a plane transverse to the alignment (and movement) (Variant 1, FIG. 5; Variant 1', FIG. 6; Variant 1b, FIG. 7; Variant 2, FIG. 8; Variant 2b, FIG. 9; Variant 2c, FIG. 10; Variant 4, FIG. 16; Variant 4b, FIG. 23) have a common longitudinal axis, which will be denoted by Z here. All the images are composed of chords perpendicular to this common axis, all the chords describing a slice of the body (one voxel thick) via a Z coordinate. Owing to the alignment in the longitudinal direction, the observations thus record a series of slices for the total volume. Even for many shapes which are concave per se, these individual slices are not concave, merely having different sizes, shapes and positions. Additional observation from the front (see e.g. Variant 5, FIG. 17) is advantageous only when the cross section is constant (which will generally be the case only for profile strands) and concave body details can be seen into only in the longitudinal direction.

With this concept, the utility of the number N of observation directions can be determined accurately. Symmetrical cross sections and uniformly distributed angles, specifically 306°/2*N, i.e. 90° for N=2 etc., will be assumed for explanation here:

Two chords of length L delimit at 90° a square of side length L as a maximal, and a 45° rotated square (i.e. half the area) and diagonal L as a minimal convex surface. The uncertainty is thus a factor of 2.

In a generalized way, it can be stated that N observation directions give a polygon with 4*N vertices, the chords between opposite vertices having the length L for 2*N of these vertices and this length lying between $L*\cos\alpha$ and $L/\cos\alpha$ for the other two, where $\alpha$ is defined as 360°/4*N. the error ratio E is therefore given as $\cos^2(\alpha)$, i.e.

for N=2, E=2.00 (see above)
for N=3, E=1.33
for N=4, E=1.17

Without prior knowledge of the product, L or the average of max and min values is accordingly the most favorable estimate. For products with particular shapes determined by plane-parallel surfaces, however, L-max may also be the more favorable value. The range between L-min and L-max is therefore preferably addressed by a matching parameter of 0-100%, which in the normal case is 50%. These considerations can be transposed to the situation of non-equidistributed angles (the use of which is however not advantageous) and non-symmetrical cross sections (which is the general case) by simple application of plane geometry.

The present invention also relates to a method for reconstructing the volume of individual particles by observation of the particles from N observation directions in a plane transverse to the alignment of the particles, the volume of the individual particles being composed of a voxel comprising thick individual slices in the form of a polygon with 4*N vertices and the cross section of the individual slices being determined by the following steps:
a) determination of the maximally possible cross section Q-MAX, preferably by joining the 2*N intersection points of the respective two maximal delimiting lines in the N observation directions, so as to obtain a polygon MAX with 2*N vertices and sides L-MAX joining the 2*N vertices;
b) determination of the minimally possible cross section Q-MIN, preferably by joining the side bisectors of the polygon with 2*N vertices obtained in step a), which forms the maximally possible cross section, so as to obtain a polygon MIN with 2*N vertices and sides L-MIN joining the 2*N vertices;
c) determination of the most probable cross section Q-OPT of a slice forming the volume of an individual particle, which has a value of at least Q-MIN and at most Q-MAX, preferably by selecting a cross section which is formed by 4*N vertices, of which 2*N are the aforementioned MIN vertices and the remaining 2*N lie on the line between the midpoints of the 2*N MIN sides and the 2*N MAX points, preferably half-way.

Determination of the values for Q-MIN, Q-MAX L-MIN and L-MAX is carried out by application of the geometry as known to the person skilled in the art.

The reconstruction method according to the invention is preferably used in step c) of the method according to the invention for automated determination of the individual three-dimensional shape of particles.

For the preferred version with 4 observation directions, a hexadecagon is obtained. This is constructed from the 8 intersection points HUAU, VOAU, VOQO, HOQO, HOAO, VUAO, VUQU and HUQU between the observation beams (see EEG FIGS. 19, 20). This octagon is the maximally possible cross-section. The 8 side midpoints 1 of this octagon form the minimally possible octagon (see FIG. 20). If an arbitrary point on the line from the 8 side midpoints of the octagon formed by the side midpoints 1 to the associated vertices HUAU, VOAU, VOQO, HOQO, HOAO, VUAO, VUQU and HUQU is additionally used as support points 2, in which case they may be shifted in a defined way with a parameter of from 0 to 100% over these distances, then the cross section can be adjusted continuously between the minimal and maximal cross section. A value of 50% is generally advantageous.

For a simpler embodiment with 2 observation directions, there is a further preferred reconstruction: a so-called reconstruction cross section is selected. To this end, two reconstruction cross sections, oval (E) or rectangular (R), are specified with knowledge of the particle to be measured. For certain known volume shapes, the program then checks the cross sections of the respective image pair therefor, and assigns them either a cross section R or a cross section E by determining a two-dimensional form factor for each particle image. This gives the combinations EE, RR, and RE or ER. The third cross section is extended automatically from the predetermined body model, e.g. RRR (cuboid), EEE (triaxial ovaloid), RRE (cylinder) or REE (cushion-shaped particle).

The present invention therefore also relates to a method for reconstructing the volume of individual particles by observation of the particles from two observation directions, generally with the aid of two cameras, which comprises the following steps:
i) selection of a reconstruction cross section by specifying two reconstruction cross sections, oval or rectangular, with knowledge of the particles to be determined,
ii) automated verification of the cross sections of the respective image pairs obtained in step b) with the aid of the predetermined reconstruction cross sections and automated allocation of one of the predetermined cross sections oval or rectangular;
iii) automated extension of the third cross section according to the specifications in i), a 2-dimensional form factor being determined for each individual particle.

The reconstruction method according to the invention is preferably used in step c) of the method according to the invention for automated determination of the individual three-dimensional shape of particles.

Imaging of the respective particle is respectively available following step cb), with reconstruction of a three-dimensional image of each particle. The three-dimensional image is preferably a voxel image.
cc) Further Evaluations Determination of the actual volume of the respective particles is difficult, since indentations (holes, trenches, cuts) and dead spaces behind outcrops in the surface of the particle can be detected only with difficulty, although they have a substantial effect on the actual volume of the particles. For determining the actual volume of each particle, the software program therefore comprises matching parameters which are assumed according to the known shape of the particles, in order to carry out corresponding extrapolations (convex correction). The undetected volume portions can be estimated from the concave portions of the projection surfaces. Various model considerations with "blackberries" and cubes carrying small cubes show that a linear model is highly suitable:

Convex portion in the volume=parameter*concave portion in the projection surface, with a corresponding matching parameter preferably of between 0.2 and 4. These values were determined by geometrical model calculations.

For simulation calculations, it is advantageous to represent the particle volume by a set of interpenetrating spheres. These spheres are determined automatically. The following procedure is preferred: the distance from the particle surface $R_0$ is determined for each voxel of the particle volume. A sphere with a radius which is preferably slightly larger (R_Draw) is drawn from the point with the highest value in a separate image memory, and the midpoint coordinates as well as the radius are stored. This sphere (or preferably a slightly smaller sphere with the radius R_Delete) is deleted from the original image. For the remaining original image, the voxel with the highest value is again looked for and the procedure is repeated until either a predetermined number of spheres is reached or a specific percentage of the original volume is reached in the new image (e.g. 98%), or the smallest permissible radius, or all of the voxels in the original image are deconstructed. These parameters are determined experimentally for previously studied products (comparison: measured volume against volume reproduced by the spheres).

The following values have been found to be suitable e.g. for a rough product with 0.3 to 3 mm particle sizes (recorded with 400 spheres):

$$R\_Draw = R_0 * CDraw + Offset$$

where CDraw takes values of between 100% and 102%, and Offset takes values of between 0.60 and 0.75 pixel $$R\_DELETE = R_0 * CDelete$$

where CDelete takes values of between 80% and 85%.

For other products and resolutions, the values should be determined according to the procedure described above.

Determination of the longest chords and other geometrical parameters is described in the literature and known to the person skilled in the art.

Another solution has been developed according to the invention for determining the surface area. The perimeter is advantageously determined in 2D images with a value table, which assigns a fixed value to each pixel combination (see Michael Schäfer; Digital Optics: Some Remarks on the Accuracy of Particle Image Analysis (p. 158-168), Part. Part. Syst. Charact. Vol. 19, Issue 3, July 2002). In 2D, a pixel has 8 neighbors so that a value needs to be assigned to 256 possible patterns.

Converting this principle into 3D is not practicable since the 26 spatial neighbors can assume 67108864 combinations in 3×3×3 proximity, and the list would be scarcely compilable and manageable. According to the invention, therefore, surface allocation is provided on the basis of 2×2×2 proximity. Which of the 256 combinations are equivalent is firstly determined, in which case it should be noted that they can be converted into one another by rotation and reflection so that there are actually only 22 different patterns. Only 3 of these basic shapes occur in X, Y, Z aligned cuboids: smooth surfaces, straight edges, corners. These values are then set for different side ratios and sizes so as to obtain exactly the geometrically correct surface. The value 0.75 is then obtained for these corners, the value 1 for these edges and likewise the value 1 for these surfaces. The remaining values are then set so as to obtain the best possible recording of spheres or other presupposed shapes. For spheres, the optimal value is e.g. 0.6 for corners, 0.8 for edges and 0.965 for surfaces. According to this rule, suitable values can be determined for all patterns. For each shape family, test bodies are generated in different parameterizations (diameter, dimensions), position and orientation but with a known surface, and evaluated with the starting values of the parameters. The parameters are then varied until the overall error is minimized. This may be done manually/interactively/intuitively, or according to known mathematical methods of error minimization.

The present invention therefore also relates to a method for determining the surface area of individual particles with the aid of 3D voxel images on the basis of a 2×2×2 proximity, which comprises the following steps:

i) determination of equivalent combinations from the total number of 256 possible combinations, 22 different patterns being determined;

the further optimization of the values for the 22 patterns may be carried out either by the standard methods known to the person skilled in the art or by the method described below comprising steps ii), iii) and iv):

ii) determination of the frequency of the individual patterns from a particular set of test bodies;

iii) optimization of the values for the individual patterns in the order of their frequency based on a value range of from 0 to 2, preferably from 0 to 1;

iv) iteration until constant values with a residual error generally of at most 2% on average, preferably at most 1% on average, so as to obtain optimal recording of the surface area of the individual particles.

The term particular set of test bodies (see ii)) is intended to mean the shape of the particles to be analyzed.

The value of the residual error (see iv)) depends inter alia on the respective test bodies.

A residual error of at most 1% on average is generally achieved for spheres.

Suitable optimization methods (see iii)) and iteration methods (see iv)) are known to the person skilled in the art.

Besides discrete volume elements such as cubic voxels, as already mentioned above, the shape of the individual particles can also be represented by finite surface elements such as triangles. For a representation using finite surface elements, the determination of the surface of the individual particles is carried out with the aid of algorithms known to the person skilled in the art, in which case an even higher accuracy can generally be achieved than in the methods for determining the surface of the individual particles on the basis of 3D voxel images.

The results of the evaluation in step c) can be used e.g. for the following tasks:

i) assessment of products with the aid of various properties (distributions, average values)

ii) assessment of products and differences with the aid of property profiles (fingerprint)

iii) determination of the correlation between the product and particle properties iv) determination of product properties and product behavior by numerical simulations, e.g. bulk density, dissolving kinetics, baking behavior, flow behavior, screening fractions

PREFERRED EMBODIMENTS OF THE PRESENT INVENTION

Particularly preferred embodiments of the present invention will be mentioned below. Nevertheless, many other embodiments can be determined easily by the person skilled in the art on the basis of the aforementioned method according to the invention and the device according to the invention. The intention is not therefore to limit the invention to the embodiments mentioned below.

The materials used in the variants (embodiments) presented below are summarized in FIG. 24.

Figure 6:
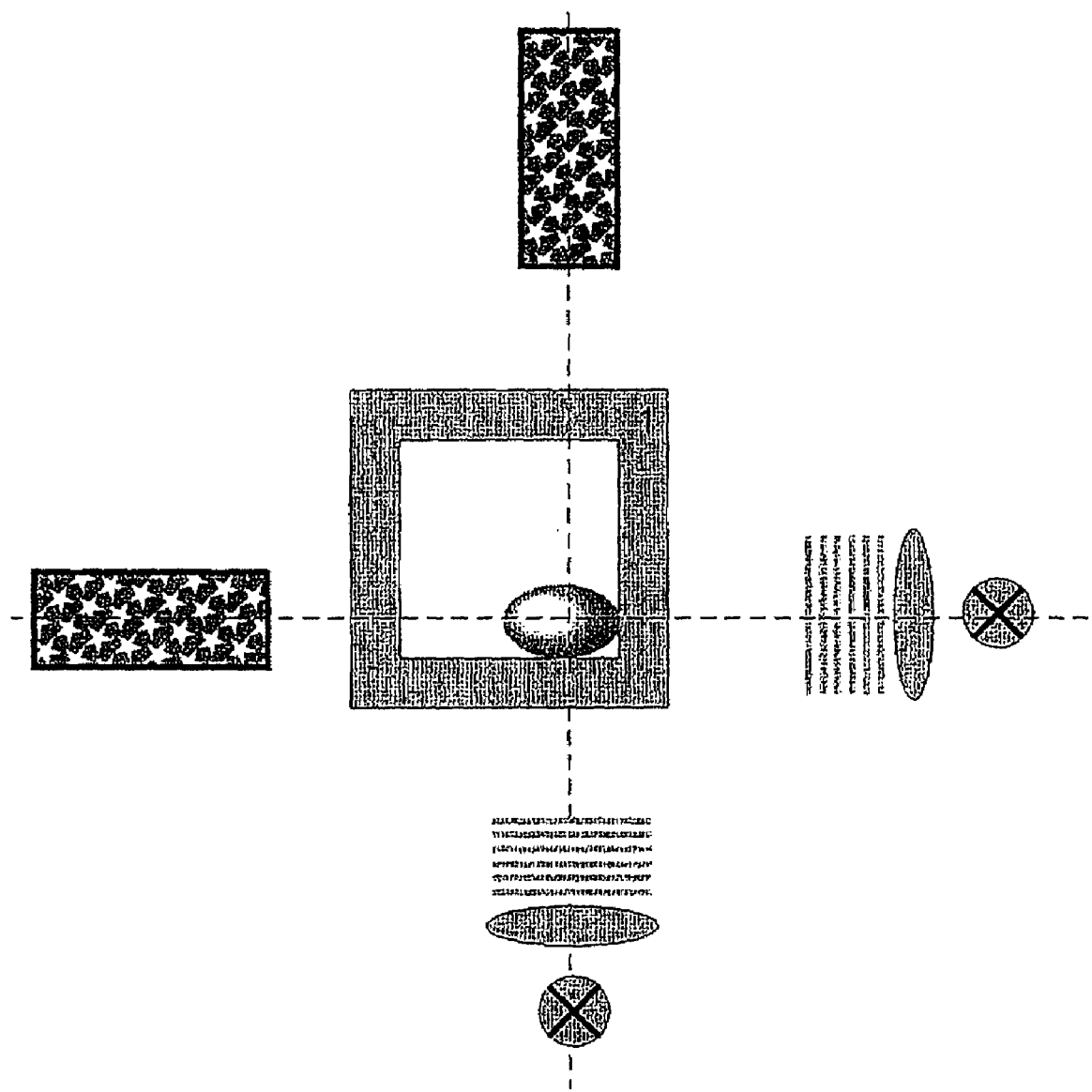
Figure 7:
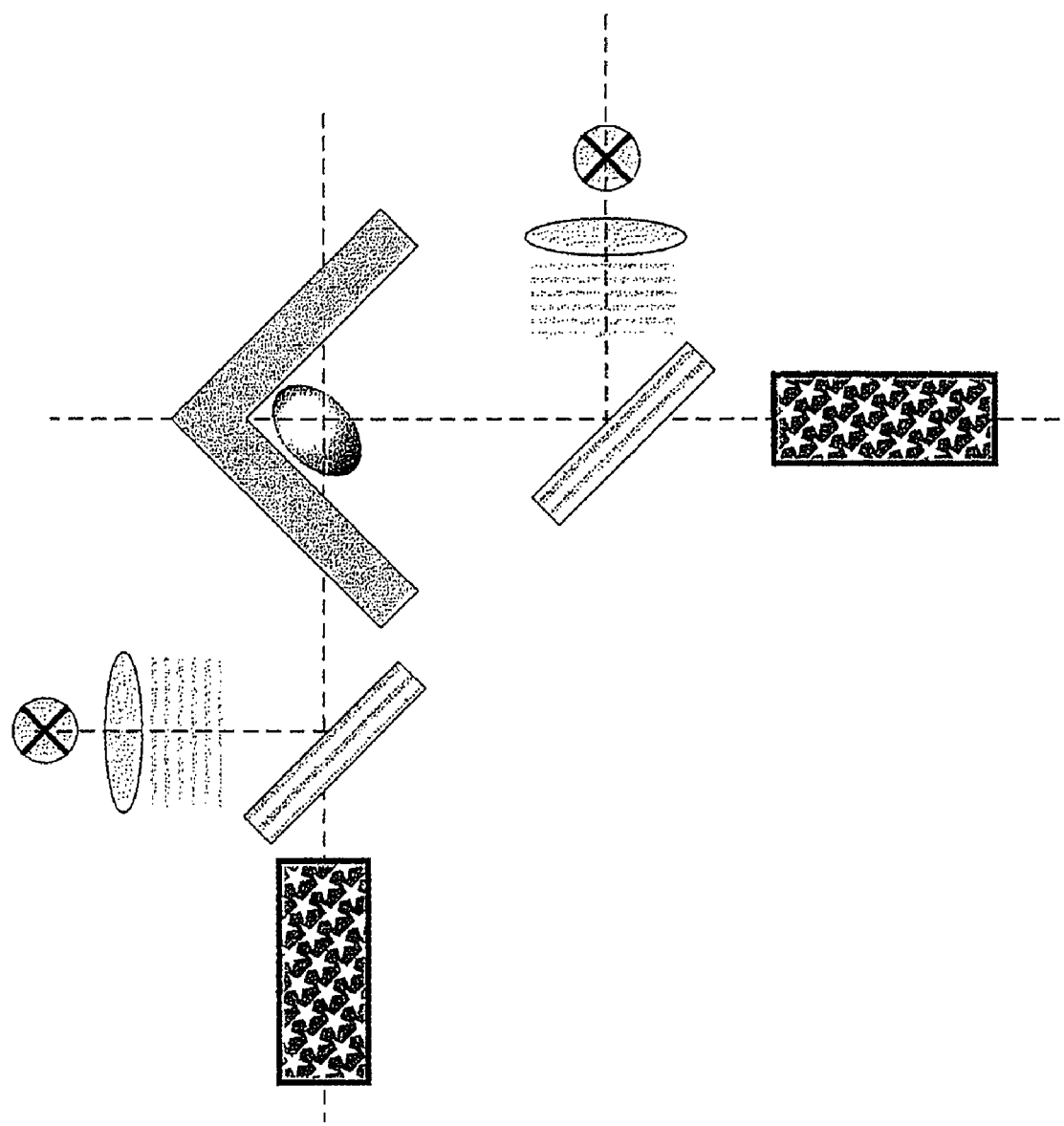

FIGS. 5 to 18 and 23 represent preferred embodiments of the present invention by way of example:

FIGS. 5 to 7 a. Simple orthogonal arrangement with 2 cameras in ETL, with square cuvette and slip delivery (Variants 1 (FIG. 5) and 1' (FIG. 6)) and as a direct light variant (Variant 1b (FIG. 7)). These variants have the advantage that they are very cost-effective.

Figure 8:
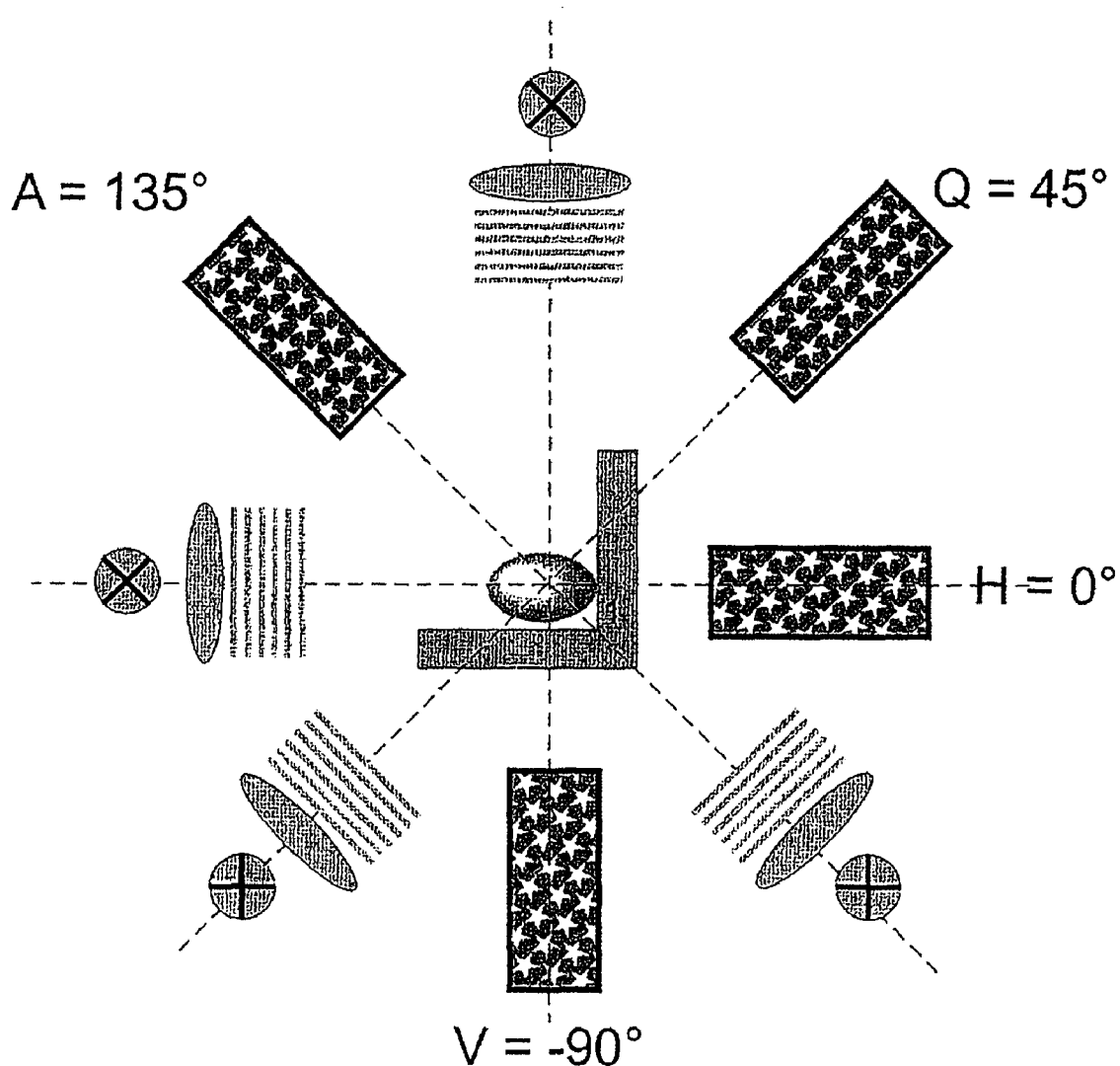
Figure 9:
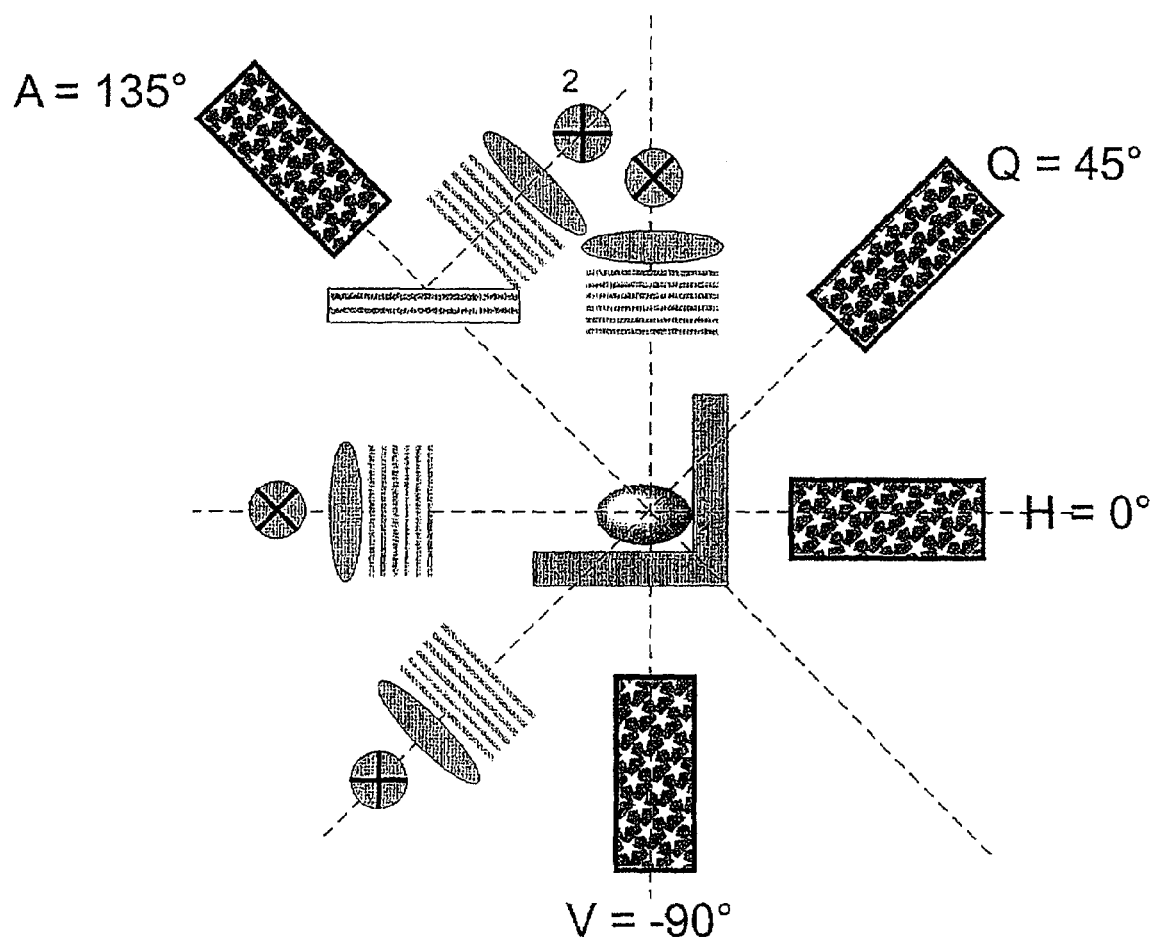
Figure 10:
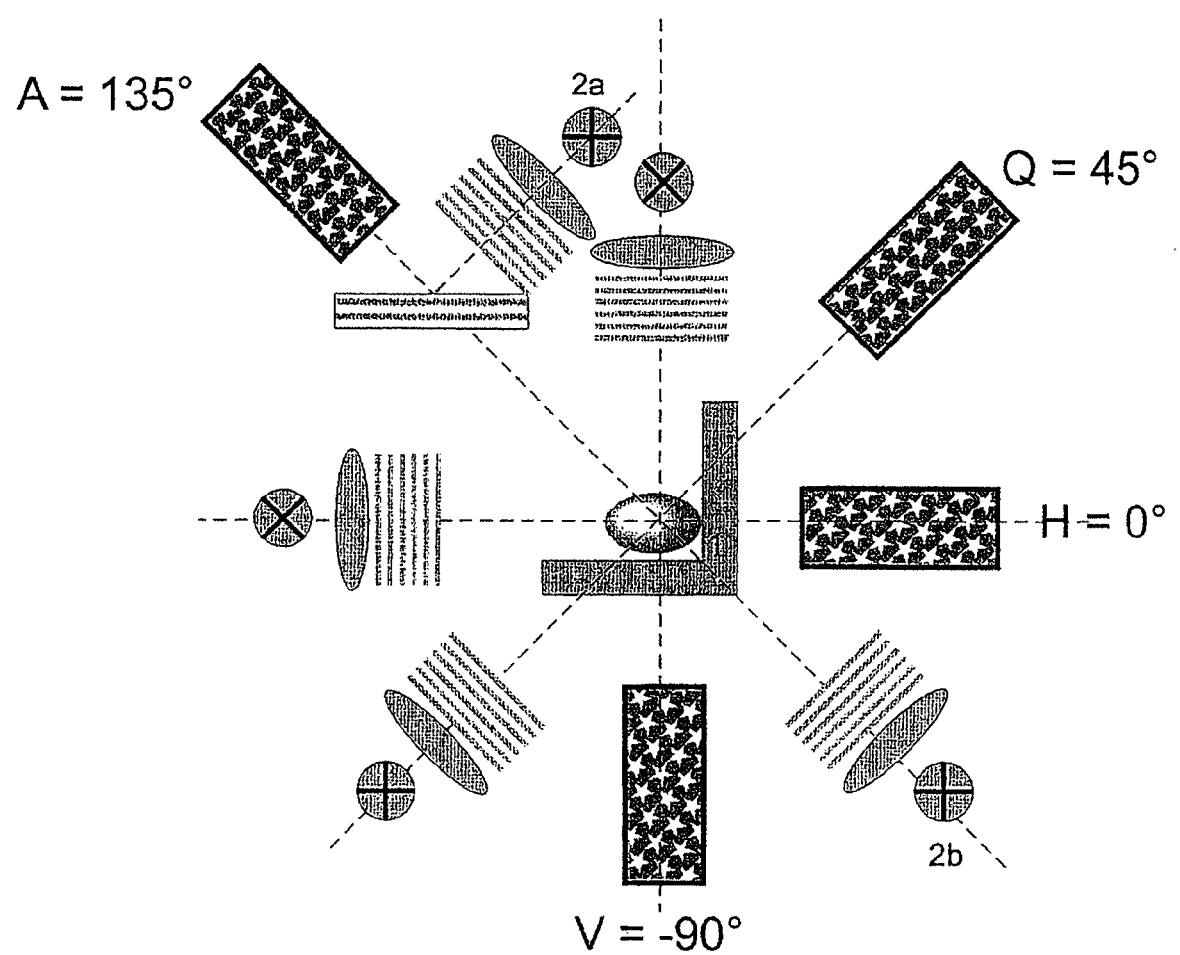

FIGS. 8 to 10 b. 0°/45°/−90°/135° arrangement with 4 cameras in a plane in ETL (Variant 2 (FIG. 8)), alternatively with 0°/90°/45° in ETL and 135° CDL (Variant 2b (FIG. 9)), respectively in right-angled glass V-channel and slip delivery. All ring profiles and arrangements represented in Variant 3 (FIGS. 11 to 15) are naturally also suitable for a transparent or white-diffusely scattering profile for a delivery channel. Two illumination paths (ETL and CDL) are set up for the 135° direction in Variant 2c (FIG. 10), which can be used selectively without refitting by switching the lamps on and off. It should be noted here that the CDL looks at 45° inclined surfaces so that there is no direct reflection. This 2c Variant is particularly preferred because it is very accurate and versatile, since the 135° direction (A) can also be equipped with a color camera (RGB) so that the color of the particle in question can also be determined.

Figure 13:
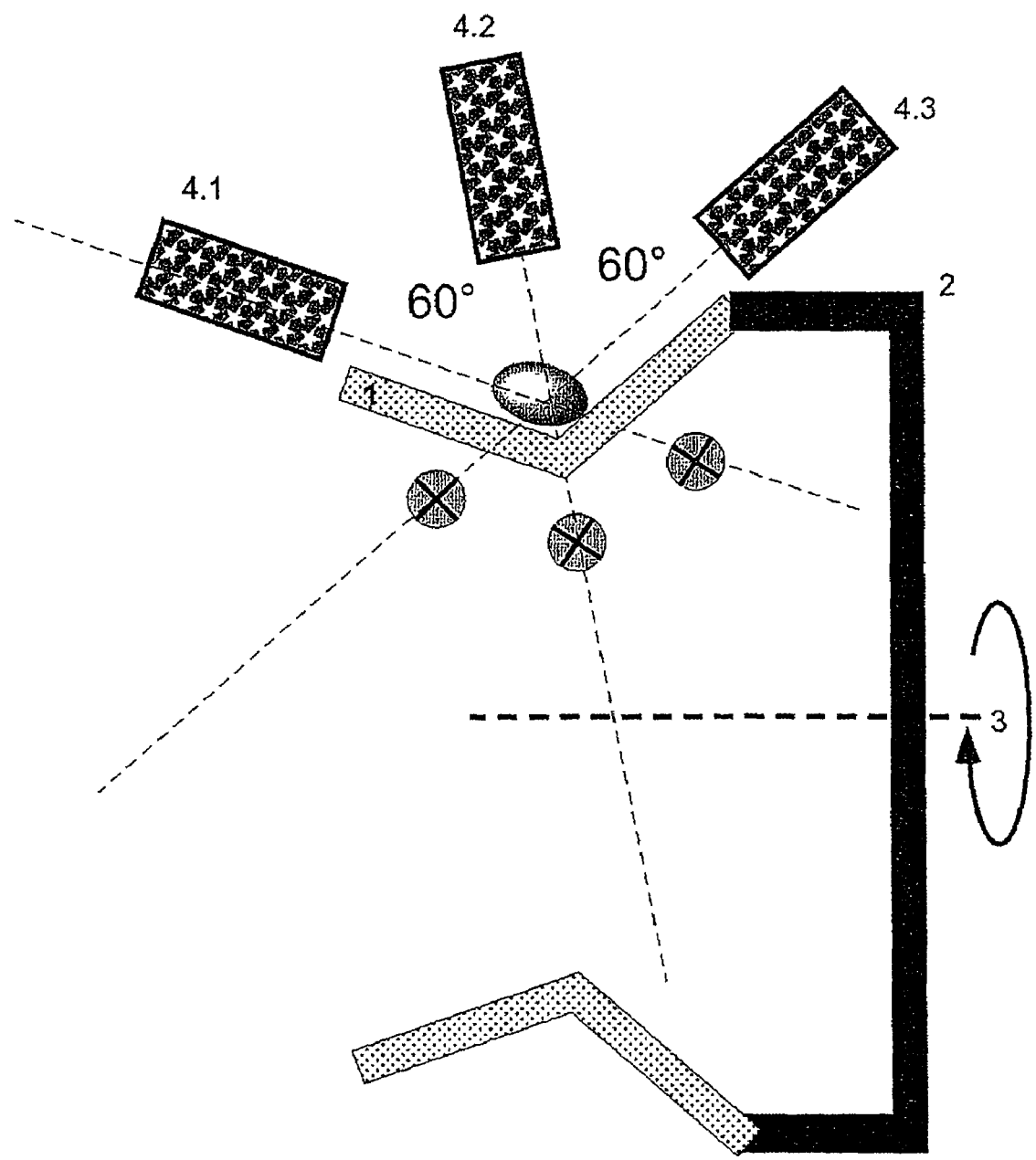
Figure 14:
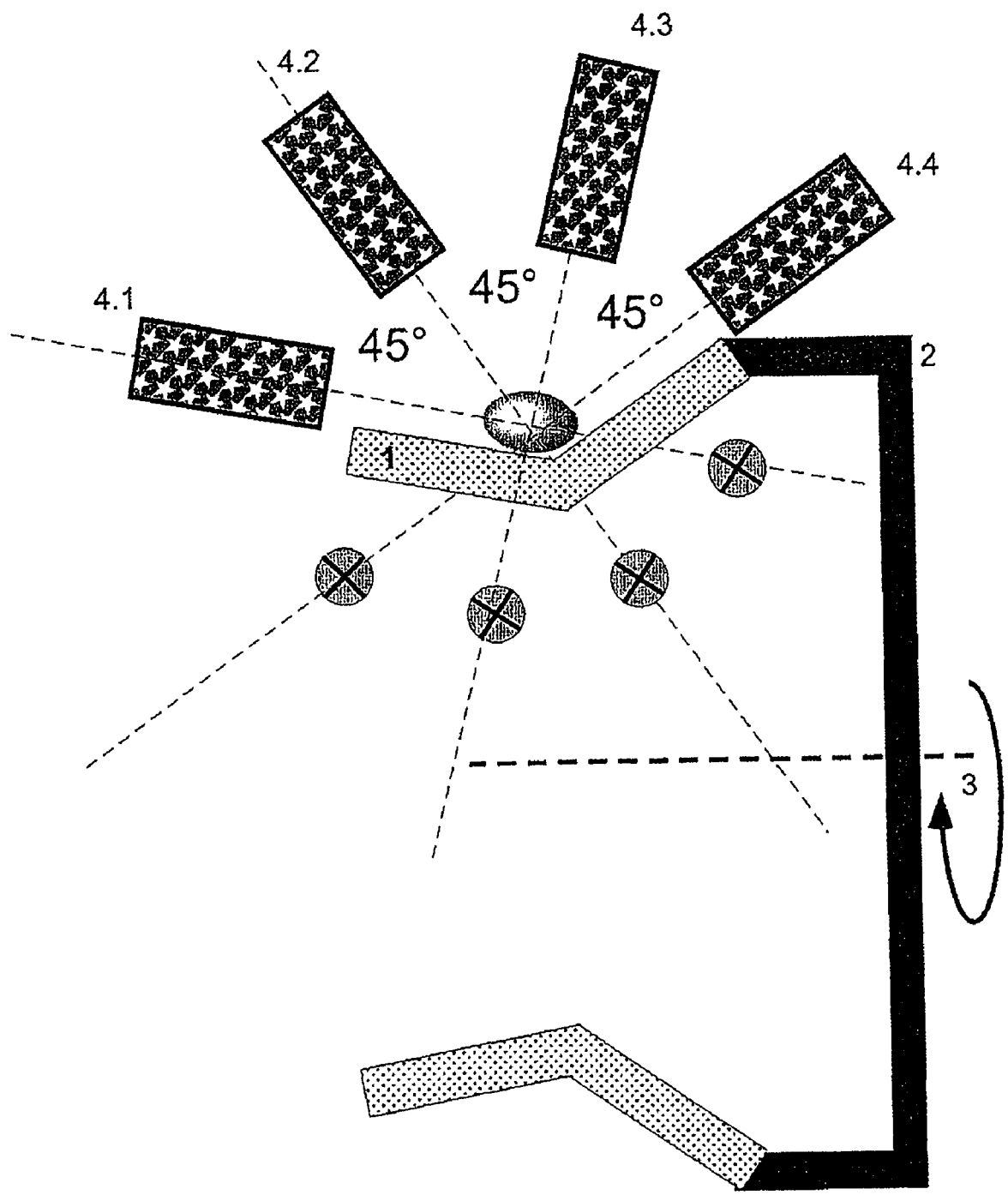
Figure 15:
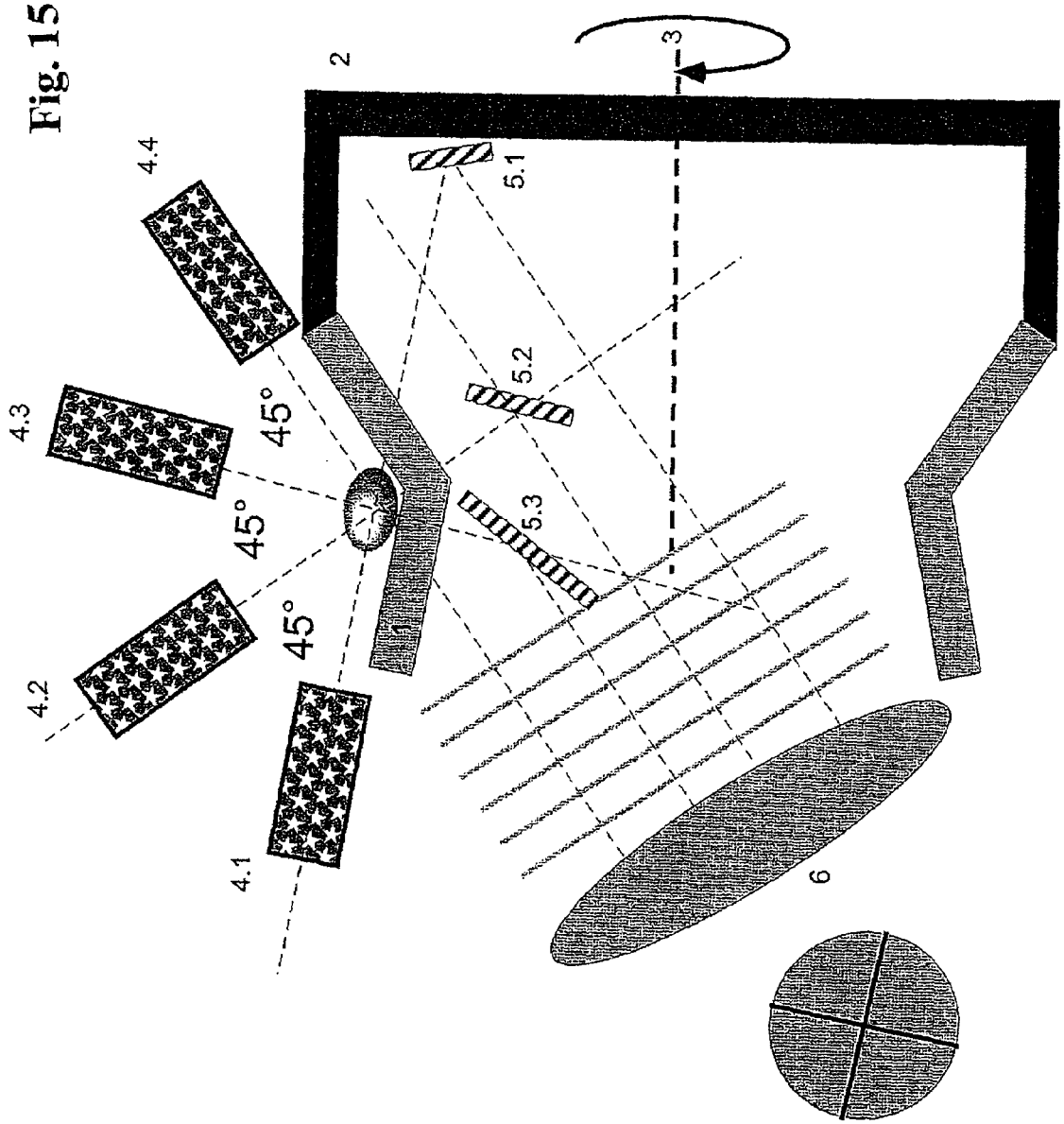

FIGS. 11 to 15 c. Simple orthogonal arrangement with 2 cameras in DTL, with a rotating cylinder and a white-diffusely scattering, background-lit 90° V-ring groove, particle deposition outward, observation on the upper pole (Variant 3-2 (FIG. 11)), alternatively deposition inward, observation on the lower pole (Variant 3-2b (FIG. 12)). More observation directions can be accommodated if the groove is selected with a larger aperture angle, 3 at an angle of 60° each in the case of 120° (Variant 3-3 (FIG. 13)), and 4 at an angle of 45° each in the case of 135° (Variant 3-4 (FIG. 14), comparable to Variant 2). Each of these variants can also be implemented in ETL, as represented for 4 directions in Variant 3-4b (FIG. 15). These variants are preferred for particles which are difficult to deliver, and can give higher particle rates owing to the predetermined delivery speed (more particles per time).

FIG. 16, FIG. 23 d. Simple orthogonal arrangement with 2 cameras in ETL and flow through a precision cuvette for suspended samples (Variant 4), optical limitation to depth of focus range and upstream biaxial alignment cell. This embodiment version cannot offer unique counting, but it is highly suitable for smaller particles no longer dosable dryly and high particle rates. Alternative arrangement with 4 cameras in a plane (0°/45°/–90°/135°) in ETL, the use of an octagonal cuvette, cross section restricted optically as in Variant 4 or by the envelope stream technique (Variant 4b).

Figure 17:
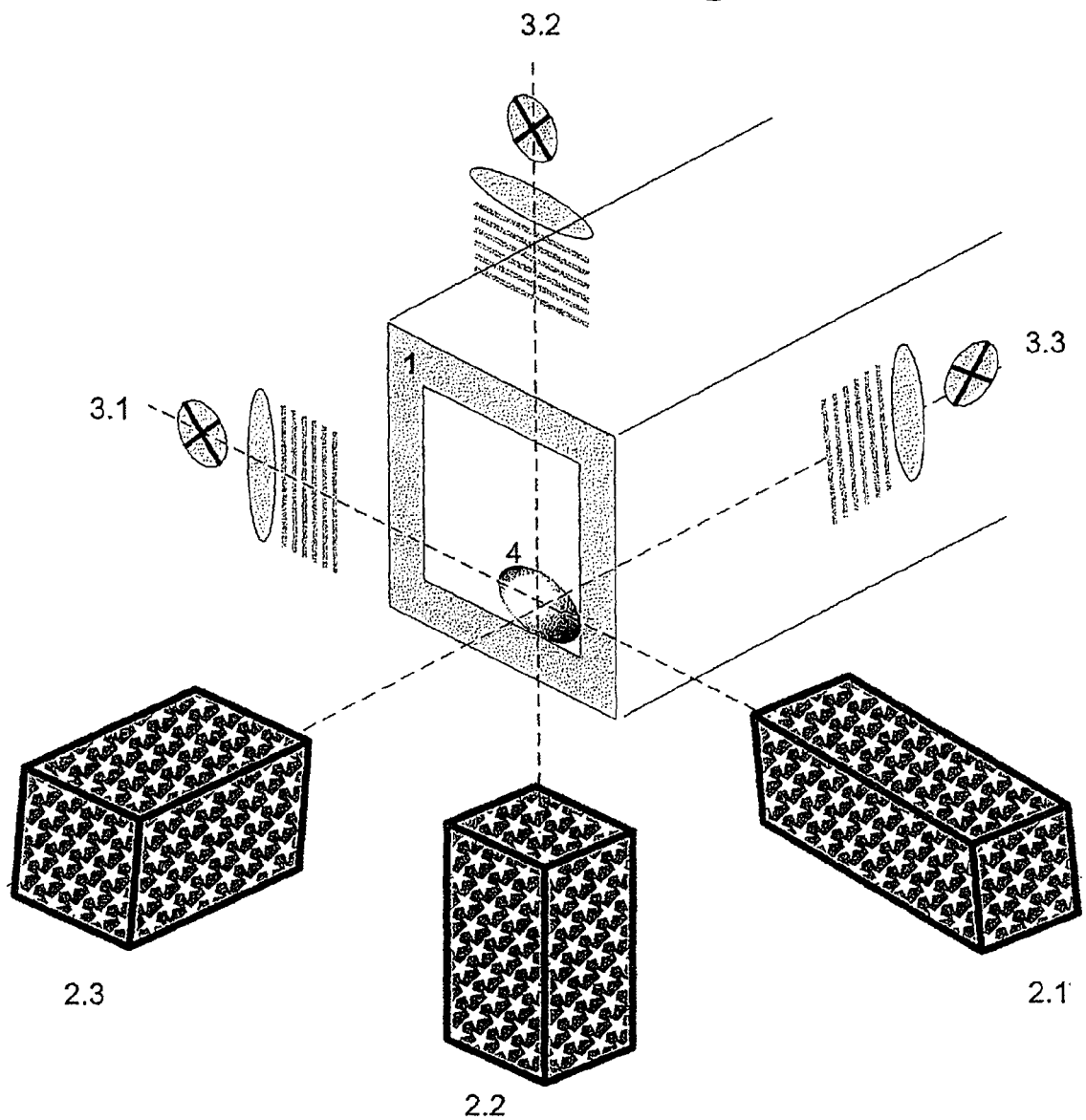
Figure 18:
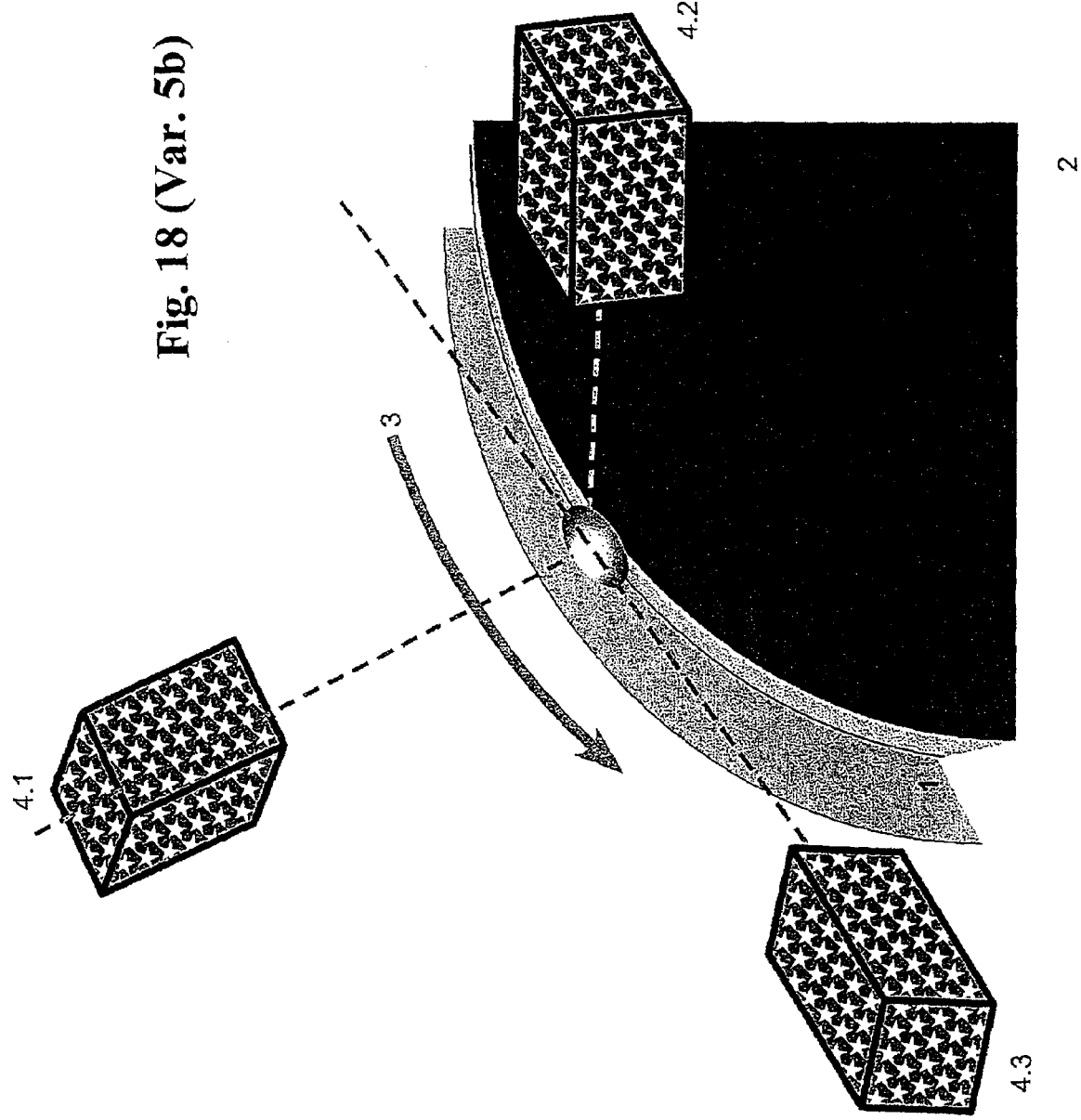

FIGS. 17 and 18 e. Spatially orthogonal arrangement (Variant 5 (FIG. 17)) with 3 observations in ETL respectively at 900 to one another, one of which looks in the delivery direction (cuvette, slip/vibration delivery), alternatively (Variant 5b (FIG. 18)) also embodied as Variant 3-2, but transparent groove ring for ETL and one tangentially arranged ETL observation. These variants may be triggered by a light barrier. These variants are preferred when the particles have a constant cross section in the longitudinal direction.

The present invention also relates to a device for automated determination of the individual three-dimensional shape of particles, comprising:

a) means for individualized dosing of the particles, means for alignment of the particles in the longitudinal axis and means for automated delivery of the particles along a predetermined line;
b) at least two cameras for observation of the aligned particles; from at least two observation directions
c) means for evaluation of the images.

FIGS. 21 and 22 represent examples of a suitable device according to the invention in different perspectives.

Suitable means for alignment of the particles and for automated delivery of the particles, means for image acquisition and means for evaluation of the images are mentioned above in respect of the method according to the invention. Instead of respectively one means for dosing, one means for aligning and one means for delivering the particles, it is also possible to use a single means for the dosing, alignment and delivery, or one means for the dosing and one means for the alignment with simultaneous automated delivery of the particles along a line. Suitable means are mentioned above.

Suitable materials for the means lying in the beam path, in particular for delivery channels and cuvettes, are mentioned above. There are no particular requirements for materials not lying in the beam path, any materials which the person skilled in the art uses for precision mechanical constructions being suitable, such as an aluminum, steel, plastic. Aluminum will mostly be used in practice. The materials used are therefore discussed only for the delivery channel/groove materials.

The present invention also relates to the use of the device according to the invention for automated determination of the individual three-dimensional shape of particles. The device according to the invention is preferably used to carry out the method according to the invention.

LIST OF REFERENCES

Figure 1:
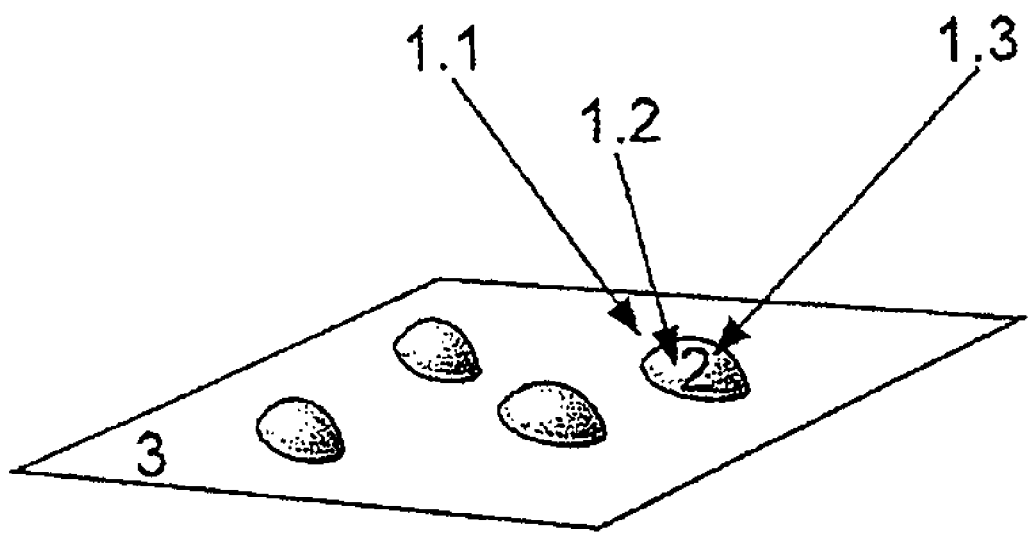
FIG. 1 shows possibilities for examining particles deposited on a flat preparation, observation being carried out from a plurality of angles.
Figure 11:
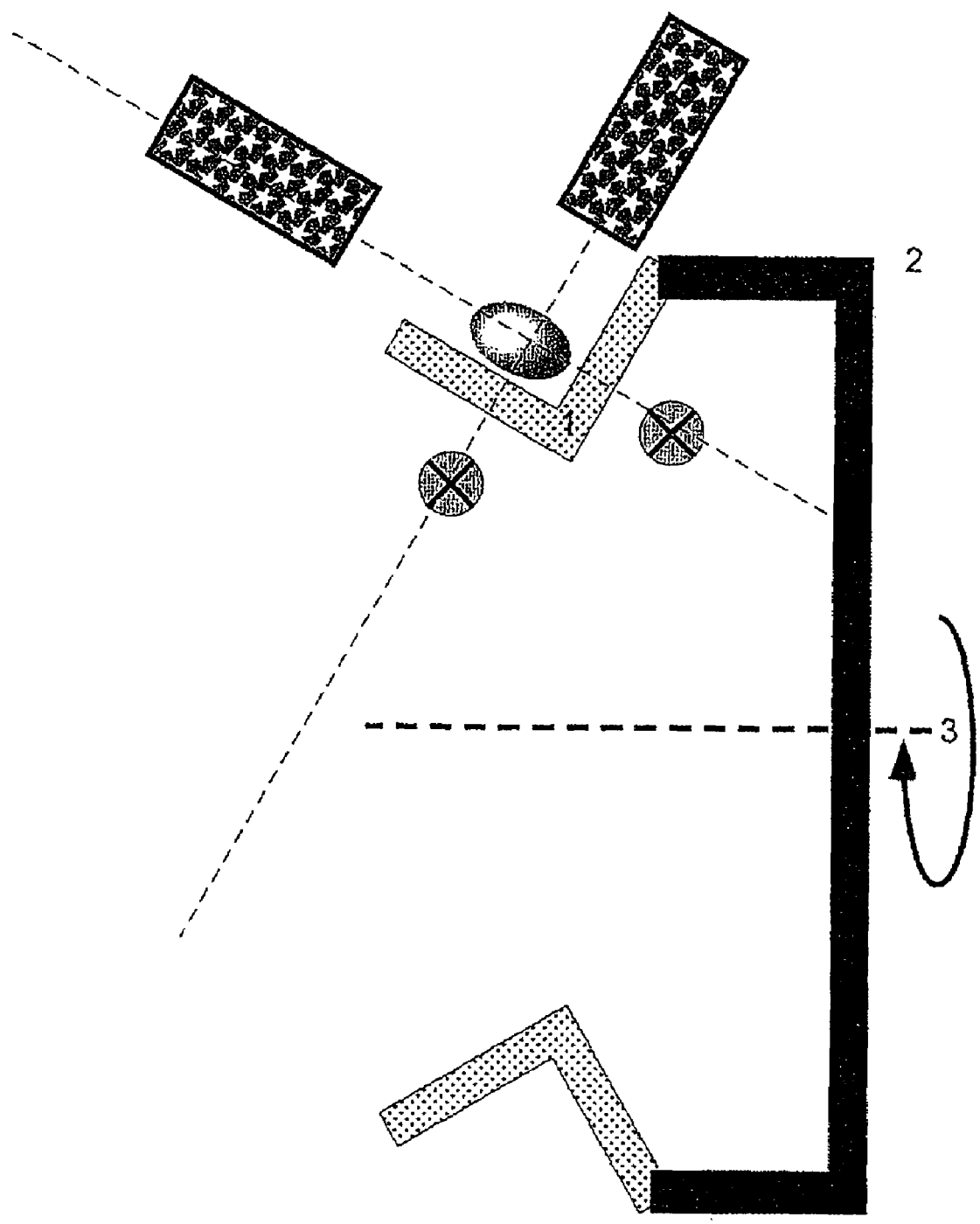
Figure 12:
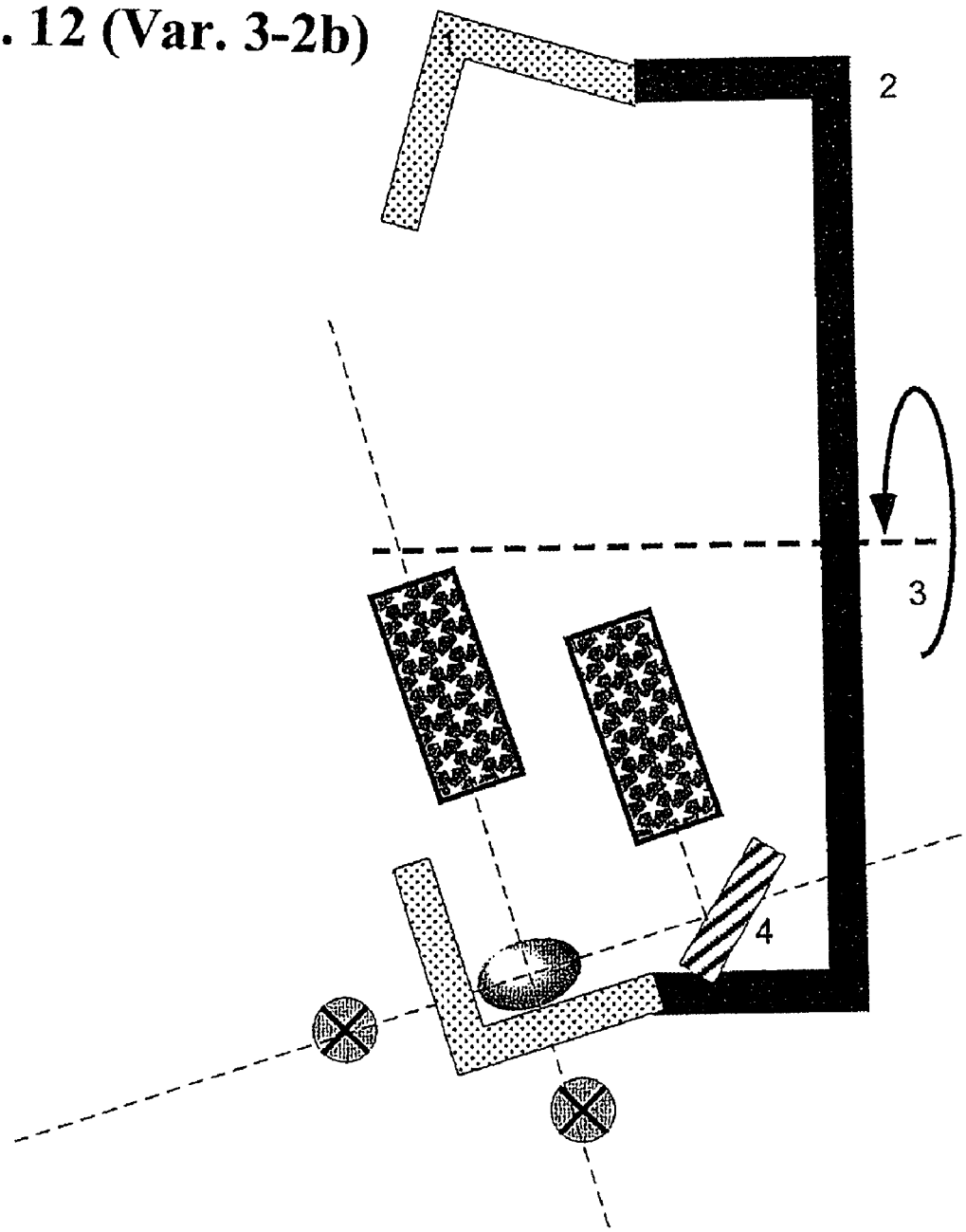
Figure 16:
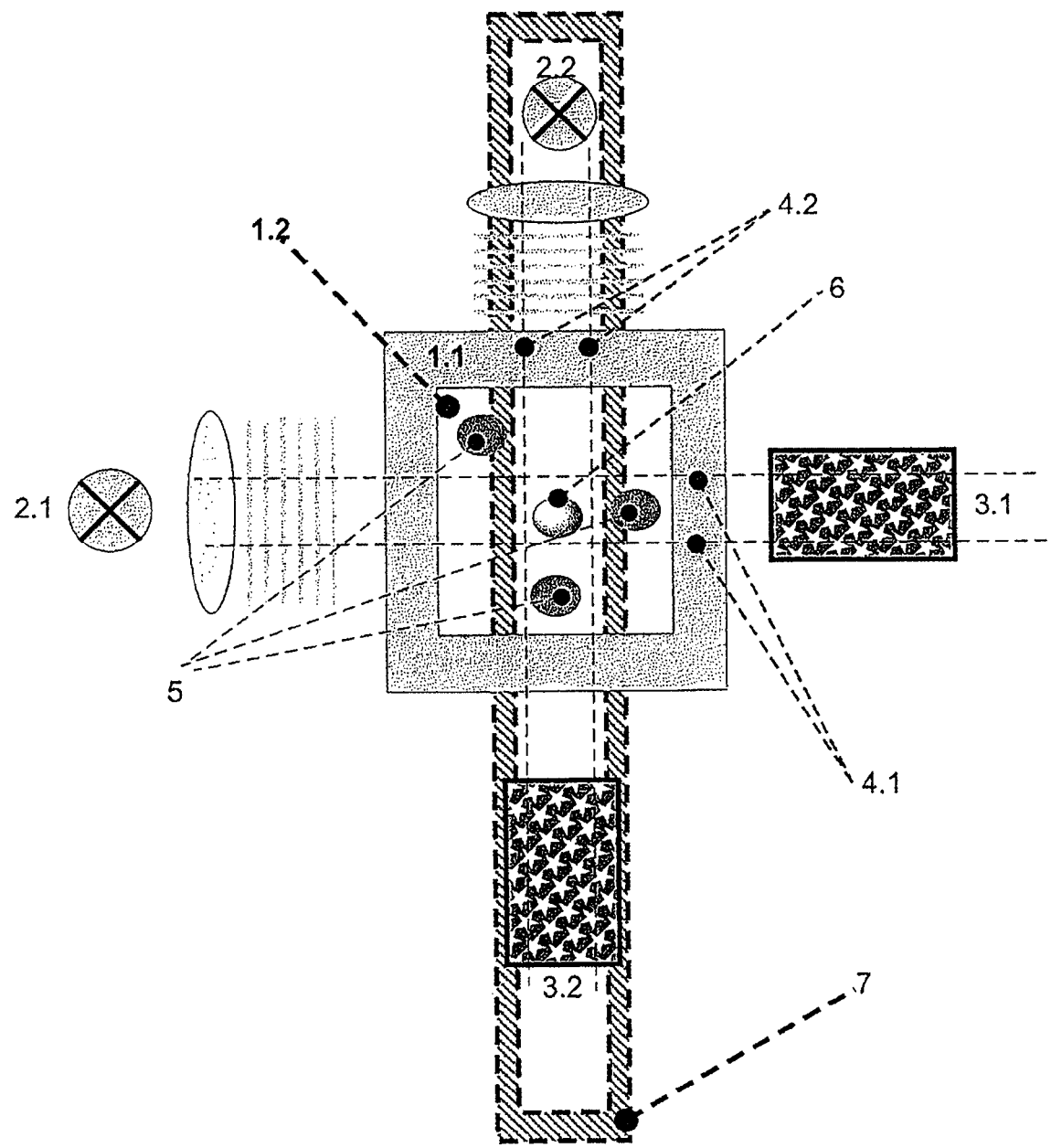

FIG. 1
1.1, 1.2, 1.3 3 observation directions for cameras
2 observed particle
3 base, plane substrate, support
FIG. 2a
1.1, 1.2, 1.3 3 observation directions for cameras
2.1, 2.2 observed particles
3 detail
4 movement direction (freefall)
FIG. 2b
1.1, 1.2, 1.3 3 observation directions for cameras
2 observed particle
3 turntable as substrate
4 movement direction rotation
FIG. 2c
1.1, 1.2, 1.3 3 observation directions for cameras
2 observed particles
3 scanning stage with support plate
4 movement direction X/Y scan
FIG. 3
1 top dosing channel (optional)
2 middle dosing channel
3 bottom dosing channel
4 support for top dosing channel
5 support for middle dosing channel
6 support for overall structure of dosing channels, displacement stage
7 baseplate for dosing channels and sensor module
8 sensor module
FIG. 4
1a, 1b commercial dosing channel, drive part
2a, 2b commercial dosing channel, V-channel
3a, 3b light barrier holder with light barrier
4a, 4b support plate for dosing channel and light barrier
5, 5a, 5b, 5c installation and views of product guide funnel
FIGS. 5, 6, 7, 8
1 cuvette as guide channel
FIG. 9
1 cuvette as guide channel
2 direct light illumination for camera A=135°
FIG. 10
1 cuvette as guide channel
2a direct light illumination for camera A=135°
2b transmitted light illumination for camera A
FIG. 11
1 white, semitransparent profile
2 support ring
3 rotation axis
FIG. 12
1 white, semitransparent profile
2 support ring
3 rotation axis
4 deviating mirror FIG. 13
1 white, semitransparent profile
2 support ring
3 rotation axis
4.1, 4.2, 4.3 3 cameras each at an angle of 60°
FIG. 14
1 white, semitransparent profile
2 support ring
3 rotation axis
4.1, 4.2, 4.3, 4.4 4 cameras each at an angle of 45°
FIG. 15
1 clear, transparent profile
2 support ring
3 rotation axis
4.1, 4.2, 4.3, 4.4 4 cameras each at an angle of 45°
5.1, 5.2, 5.3 deviating mirror for the respective camera
6 parallel illumination with large aperture
FIG. 16
1.1 transparent cuvette at observation position
1.2 cuvette cross section flowed through
2.1 illumination for camera 1
2.2 illumination for camera 2
3.1 camera 1
3.2 camera 2
4.1 image detail taken into account by camera 1
4.2 image detail taken into account by camera 2
5 particles not taken into account
6 particles taken into account (measured)
7 entry cross section of the flow in the upstream alignment feed (biaxial extent)
FIG. 17
1 transparent cuvette at observation position
2.1 camera 1
2.2 camera 2
2.3 camera 3
3.1 illumination for camera 1
3.2 illumination for camera 2
3.3 illumination for camera 3, coaxial in cuvette
4 measured particle
FIG. 18
1 transparent V-profile, illuminated from inside
2 rotating support disk for V-profile
3 rotation direction
4.1, 4.2 camera transverse to the rotation direction, tangential to the profile flanks
4.3 camera transverse to the circumference (groove bottom)
FIG. 19
M coordinate reference point for all images, cuvette vertex
H observational direction horizontal, or parallel to one bearing surface
V observational direction vertical, or parallel to the other bearing surface
Q observation direction transverse, i.e. both bearing surfaces at 45°
A direct view, i.e. view into the recess or into the V-channel
HU, HO upper and lower borders of the H-image
VU, VO see above
QU, QO see above
AU, AO see above
HUVU, . . . point of intersection between HU and VU, the 4 points HUVU, HUVO, HOVU, HOVO form the rectangle which circumscribes the maximal cross section of the images H and V. The further points HUAU, VOAU, VOQO, HOQO, HOAO, VUAO, VUQU and HUQU give an octagon which indicates the maximal cross section bounded by all 4 images FIG. 20
HUVU, . . . HUAU, VOAU, VOQO, HOQO, HOAO, VUAO, VUQU and HUQU give an octagon MAX which indicates the maximal cross section bounded by all 4 images
1 The midpoints of the distances between respectively two of the upper points (MAX) form an octagon MIN, which indicates the minimal cross section bounded by 4 images
2 A line can be drawn to the associated MAX point from the midpoints of the distances between respectively two of the upper points (MIN). A further support point of the polygon can be placed along each of these distances. The point 2 at 50% of the distance from the minimum to the maximum (HOQO) is shown.
3 The resulting hexadecagon represents an interpolation between the maximally possible and minimally possible cross section. The middle (50%) is shown, all values between 0% and 100% being possible. 50% is a good assumption without product knowledge, but other values may be preferred with more knowledge about product properties.
FIG. 21
1 Funnel from the bottom dosing channel to the inlet into the delivery channel (cuvette)
2 drive for the delivery channel (loudspeaker with thrust rod)
3 height adjustment for drive
4 foot of the sensor with swivel axis and angle scale
5 height adjustment of the cuvette support
6 side adjustment of the cuvette support (elastic band suspension)
7 oscillating cuvette suspension
8 cuvette or V-channel
9 holder ring for rotatable optics block
10 optics block (FIG. 22)
FIG. 22
1A camera of the A-direction
2A objective of the A-direction
3A centering frame for A-camera
4A stop for A-camera
5A focus drive for A-camera
6A illumination optics for A-direction
7A condenser A
8A diffuser disk/filter A
9A cooling block and adjusting frame for light source A
10A semitransparent mirror for direct light illumination (only at A)
11 cuvette, delivery channel or V-channel seen in delivery direction, inner edge coincides with optical axes
12 support body with receiving bores for cameras and illuminations
FIG. 23
1 octagonal cuvette
2 cross section delimited optically (as in a Var. 4 (FIG. 16)) or by envelope stream technique
FIG. 24
1 transparent, clear material
2 white, diffusely scattering material
3 mirror, 100%
4 mirror, semitransparent
5 opaque material, metal
6 camera, observation
7 illumination, parallel
8 illumination, divergent
9 particle

We claim:

1. A method for automated determination of an individual three-dimensional shape of particles of samples in powder form or in a form of dispersions, comprising in succession:
   a) individualized dosing of the particles, aligning the particles in the longitudinal axis, and automated delivering of the particles along a line;
   b) observing the aligned particles from at least two observation directions and image acquisition wherein the observing is carried out by extinction transmitted light, diffuse transmitted light, coaxial direct light, or concentric direct light by at least two cameras, which are CCD or CMOS cameras;
   c) evaluating the images,
   wherein the aligning and automated delivering of the particles of samples in the form of dispersions is carried out in a flow cell for aligning particles in two axes, comprising a feed zone for the samples containing particles to be aligned and an outlet for the samples containing particles aligned in two axes, a fluid element of the samples with dimensions a, b, c being converted in a stretching zone into a fluid element with dimensions a×n, b/(n×m), c×m, where a denotes width, b denotes height, c denotes length of the fluid element, and n and m are constants (degree of stretching) depending on a geometry of the flow cell, which denote positive numbers $\geq 1$,
   or
   in a cuvette which is hexagonal or octagonal.

2. The method as claimed in claim 1, wherein the dosing of the particles of samples in powder form is carried out with aid of dosing channels.

3. The method as claimed in claim 1, wherein the alignment of particles of samples in powder form is carried out against one or more plane surfaces that form a delivery channel, with aid of gravity or with centrifugal forces.

4. The method as claimed in claim 3, wherein precision cuvettes or V-channels are used as the delivery channel.

5. The method as claimed in claim 1, wherein the particles of samples that are present in the form of dispersions are guided through a small thread of flow that is embedded in a flow through a larger opening.

6. The method as claimed in claim 1, wherein the automatic delivery of the particles of samples in powder form is carried out either by the particles sliding along a line along an intersection line of two surfaces forming a delivery channel or by the particles being deposited on a moved intersection line of two surfaces forming a delivery channel.

7. The method as claimed in claim 1, wherein the automatic delivery of the particles of samples that are present in the form of dispersions is carried out by a pump or a pressure gradient.

8. The method as claimed in claim 1, wherein the observing is carried out from 2, 3, or 4 observation directions.

9. The method as claimed in claim 1, wherein the particles of samples that are present in the form of dispersions are observed at 4 angles in an octagonal flow cell.

10. The method as claimed in claim 8, wherein an angle between the observation directions is 90° when there are two observation directions.

11. The method as claimed in claim 8, wherein the observation directions lie in a plane perpendicular to a delivery direction of the particles when there are 3 or 4 observation directions.

12. The method as claimed in claim 1, wherein images obtained in the step b) are preprocessed.

13. The method as claimed in claim 1, further comprising reconstructing a volume of the particles, individually.

14. A method as claimed in claim 13, wherein the reconstructing the volume of individual particles by observing the particles from N observation directions in a plane transverse to the alignment of the particles, the volume of the individual particles being composed of a voxel comprising thick individual slices in a form of a polygon with 4*N vertices and a cross section of the individual slices being determined by:
   a) determination of maximally possible cross section Q-MAX;
   b) determination of minimally possible cross section Q-MIN; and
   c) determination of most probable cross section Q-OPT of a slice forming the volume of an individual particle, which has a value of at least Q-MIN and at most Q-MAX.

15. A method as claimed in claim 13, wherein the reconstructing the volume of individual particles is carried out by observing the particles from two observation directions, which comprises:
   i) selecting a reconstruction cross section by specifying two reconstruction cross sections, oval or rectangular, with knowledge of the particles to be determined,
   ii) automated verifying of the two reconstruction cross sections of respective image pairs obtained in the step b) with aid of the two reconstruction cross sections and automated allocating of one of the two reconstruction cross sections oval or rectangular; and
   iii) automated extending of a third cross section according to the specifying in the step i), a 2-dimensional form factor being determined for each individual particle.

16. A method according to claim 1, wherein the evaluating in the step c) is a determination of surface area of individual particles with aid of 3D voxel images on a basis of a 2×2×2 proximity, which comprises:
   i) determining equivalent combinations from a total number of 256 possible combinations, 22 different patterns being determined;
   ii) determining frequency of individual patterns from a particular set of test bodies;
   iii) optimizing values for the individual patterns in order of their frequency based on a value range of from 0 to 2; and
   iv) iterating until constant values with a residual error of at most 2% on average, so as to obtain optimal recording of the surface area of the individual particles.

17. A device for automated determination of the individual three-dimensional shape of particles, comprising:
   a) means for individualized dosing of the particles, means for aligning the particles in the longitudinal axis, and means for automated delivery of the particles along a predetermined line;
   b) at least two cameras that observe the aligned particles, from at least two observation directions by extinction transmitted light, diffuse transmitted light, coaxial direct light, or concentric direct light, wherein the at least two cameras are CCD or CMOS cameras;
   c) means for evaluating the images,
   wherein the aligning and automated delivery of the particles of samples in a form of dispersions is carried out in a flow cell for aligning particles in two axes, comprising a feed zone for the samples containing particles to be aligned and an outlet for the samples containing particles aligned in two axes, a fluid element of the samples with dimensions a, b, c being converted in a stretching zone into a fluid element with dimensions a×n, b/(n×m), c×m, where a denotes width, b denotes height, c denotes length of the fluid element, and n and m are constants (degree of stretching) depending on a geometry of the flow cell, which denote positive numbers ≧1, or in a cuvette which is hexagonal or octagonal.

18. The process of claim 1, wherein the steps a), b), and c) are performed by a device comprising:

means for individualized dosing of the particles;
means for aligning the particles in the longitudinal axis;
means for automated delivery of the particles along the line;
the at least two cameras; and
means for evaluating the images.

* * * * *